US010309968B2

(12) United States Patent
Tran et al.

(10) Patent No.: US 10,309,968 B2
(45) Date of Patent: Jun. 4, 2019

(54) METHODS AND SYSTEMS FOR ASSEMBLY OF PROTEIN SEQUENCES

(71) Applicant: BIOINFORMATICS SOLUTIONS INC., Waterloo (CA)

(72) Inventors: Ngoc Hieu Tran, Waterloo (CA); Mohammad Ziaur Rahman, Waterloo (CA); Lin He, Waterloo (CA); Lei Xin, Waterloo (CA); Baozhen Shan, Waterloo (CA); Ming Li, Waterloo (CA)

(73) Assignee: BIOINFORMATICS SOLUTIONS INC., Waterloo, ON (CA)

( * ) Notice: Subject to any disclaimer, the term of this patent is extended or adjusted under 35 U.S.C. 154(b) by 183 days.

(21) Appl. No.: 15/599,431

(22) Filed: May 18, 2017

(65) Prior Publication Data

US 2017/0336419 A1   Nov. 23, 2017

Related U.S. Application Data

(60) Provisional application No. 62/338,279, filed on May 18, 2016.

(51) Int. Cl.
| | | |
|---|---|---|
| G01N 33/68 | (2006.01) | |
| G06F 19/22 | (2011.01) | |
| G06F 19/26 | (2011.01) | |
| G06F 19/24 | (2011.01) | |

(52) U.S. Cl.
CPC ..... *G01N 33/6818* (2013.01); *G01N 33/6848* (2013.01); *G01N 33/6854* (2013.01); *G06F 19/22* (2013.01); *G06F 19/24* (2013.01); *G06F 19/26* (2013.01); *G01N 2560/00* (2013.01)

(58) Field of Classification Search
None
See application file for complete search history.

(56) References Cited

PUBLICATIONS

Han, Y. et al., "SPIDER: Software for Protein Identification from Sequence Tags Containing De Novo Sequencing Error", J. Bioinform. Comput. Biol. 3(3),697-716 (2005).
Pham, V. et al., "De Novo Proteomic Sequencing of a Monoclonal Antibody Raised Against OX40 Ligand", Anal. Biochem. 352, 77-86 (Feb. 1, 2006).
Ma, B. et al., "PEAKS: Powerful Software for Peptide De Novo Sequencing by Tandem Mass Spectrometry", Rapid Commun. Mass. Spectrom. 17(20), 2337-2342 (Aug. 21, 2003).
Chi, H. et al., "pNovo: De Novo Peptide Sequencing and Identification Using HCD Spectra", J. Proteome Res., 9(5), 2713-2724 (Mar. 1, 2010).

(Continued)

*Primary Examiner* — Xiaoyun R Xu

(57) ABSTRACT

Methods and systems for determining amino acid sequence of a polypeptide or protein from mass spectrometry data is provided, using a weighted de Bruijn graph. Extracted and purified protein is cleaved into a mixture of peptide and then analyzed using mass spectrometry. A list of peptide sequences is derived from mass spectrometry fragment data by de novo sequencing, and amino acid confidence scores are determined from peak fragment ion intensity. A weighted de Bruijn graph is constructed for the list of peptide sequences having node weights defined by k-1 mer confidence scores. At least one contig is assembled from the de Bruijn graph by identifying node weights having the highest k-1 mer confidence scores.

31 Claims, 12 Drawing Sheets

Specification includes a Sequence Listing.

(56) References Cited

PUBLICATIONS

Frank, A. et al., "PepNovo: De Novo Peptide Sequencing Via Probabilistic Network Modeling", Anal. Chem. 77(4), 964-973 (Jan. 13, 2005).

Zhang J. et al. "PEAKS DB: De Novo Sequencing Assisted Database Search for Sensitive and Accurate Peptide Identification", Mol. Cell. Proteomics 10.1074/mcp.M111.010587 (2011).

Eng, J.K. et al., "An Approach to Correlate Tandem Mass Spectral Data of Peptides with Amino Acid Sequences in a Protein Database", J. Am. Soc. Mass Spectrom. 5(11), 976-898 (Jun. 29, 1994).

Cottrell, J.S. et al., "Probability-Based Protein Identification by Searching Sequence Databases Using Mass Spectrometry Data", Electrophoresis, 20(18), 3551-3567 (Aug. 27, 1999).

Geer, L.Y. et al., "Open Mass Spectrometry Search Algorithm", J. Proteome Res. 3(5), 958-964 (Feb. 23, 2004).

Craig, R. et al., "R.C. Tandem: Matching Proteins With Tandem Mass Spectra", Bioinformatics 20(9), 1466-1467 (Feb. 19, 2004).

Cox, J. et al., "Andromeda: A Peptide Search Engine Integrated Into the MaxQuant Environment", J. Proteome Res. 10(4), 1794-1805 (Jan. 21, 2011).

Grabherr, M.G. et al., "Full-Length Transcriptome Assembly From RNA-Seq Data Without a Reference Genome", Nat. Biotechnol. 29, 644-652 (May 15, 2011).

Bandeira, N. et al., "Shotgun Protein Sequencing by Tandem Mass Spectra Assembly", Anal. Chem. 76, 7221-7233 (Sep. 8, 2004).

Bandeira, N. et al., "Protein Identification by Spectral Networks Analysis", Proc. Natl. Acad. Sci. USA 104, 6140-6145 (Feb. 9, 2007).

Bandeira, N. et al., "Automated De Novo Protein Sequencing of Monoclonal Antibodies". Nat. Biotechnol. 26, 1336-1338 (Dec. 2008).

Guthals, A. et al., "Sequencing-Grade De Novo Analysis of MS/MS Triplets (CID/HCD/ETD) From Overlapping Peptides", J. Proteome Res. 12, 2846-2857 (May 16, 2013).

Guthals, A. et al., "Shotgun Protein Sequencing With Meta-contig Assembly", Mol. Cell. Proteomics, 11(10), 1084-96 (2012).

Bandeira, N. et al., "Shotgun Protein Sequencing: Assembly of Peptide Tandem Mass Spectra From Mixtures of Modified Proteins", Mol. Cell. Proteomics, 6(7), 1123-1134 (2007).

Vyatkina K. et al., "De Novo Sequencing of Peptides from Top-Down Tandem Mass Spectra", J. Proteome Res. 14(11),4450-62, (Sep. 28, 2015).

Liu, X. et al., "Automated Protein (Re)Sequencing With MS/MS and a Homologous Database Yields Almost Full Coverage and Accuracy", Bioinformatics, 25(17), 2174-2180 (Jun. 17, 2009).

Castellana, N.E. et al., "Template Proteogenomics: Sequencing Whole Proteins Using an Imperfect Database", Mol. Cell. Proteomics, 9(6), 1260-1270 (2010).

Liu, X. et al., "De Novo Protein Sequencing by Combining Top-Down and Bottom-Up Tandem Mass Spectra", J. Proteome Res., 13(7), 3241-3248 (May 30, 2014).

Compeau, P.E. et al., "How to Apply de Bruijn Graphs to Genome Assembly", Nat. Biotechnol. 29, 987-991 (Nov. 2011).

Zerbino, D.R. et al., Velvet: Algorithms for De Novo Short Read Assembly Using De Bruijn Graphs. Genome Res. 18(5), 821-9, (Mar. 18, 2008).

- Sequence Human_HeavyChain: unnamed protein product
- Alignments, Subtracks: 3 on, 0 off
  - seq0 x Human_HeavyChain, 1 entry [blastp], total 1 object ...
  - seq1 x Human_HeavyChain, 1 entry [blastp], total 1 object ...
  - seq3 x Human_HeavyChain, 1 entry [blastp], total 1 object ...

(B)

- Sequence Human_HeavyChain: unnamed protein product
- Alignments, total 1 object shown (C)

```
Sbjct   1    EVPLKESGPTLVKPTQTLTLTCSFSGFSLTTDEVGVAWIRQPPGKALEWLAVLYGDDDKR   60
Query   1    XVPLKESGPTLVKPTQTLTLTCSFXXFSLTTDEVGVAWXRQPPGKALEWXAXLYGXDDKR   60

Sbjct   61   YSPSLKSRLSITKDSSKNQVVLTMTSLDPVDTGTYYCARTRDY--------FDYWGQGTL  112
Query   61   YSPSLKSRLSXTKDSSRNQVVLTMTSLDPVDTGTYYCARTRDYXXXXXXXXFDYWGQGTL  120

Sbjct   113  LTVSSASTKGPSVFPLAPSSKSTSGGTAALGCLVKDYFPEPVTVSWNSGALTSGVHTFPA  172
Query   121  LTVSSASTXXPSVFPLAPSSKSTSGGTAALGCLVKDYFPEPVTVSWNSGALTSGVHTFPA  180

Sbjct   173  VLQSSGLYSLSSVVTVPSSSLGTQTYLCNVNHKPSNTKVDKRVEPKSCDKTHTCPPCPAP  232
Query   181  VLQSSGLYSLSSVVTVPSSSLGTQTYLCNVNHKPSNTKVDKRVEPKSCDKTHTCPPCPAP  240

Sbjct   233  ELLGGPSVFLFPPKPKDTLMLSRTPEVTCVVVDVSHEDPEVKFNWYVDGVEVHNAKTKPR  292
Query   241  ELLGGPSVFLFPPKPKDTLMLSRTPEVTCVVVDVSHEDPEVKFNWYVDGVEVHNAKTKPR  300

Sbjct   293  EEQYNSTYRVVSVLTVLHQDWLNGKEYKCKVSNKALPAPLEKTLSKAKGQPREPQVYTLP  352
Query   301  EEQYNSTYRVVSVLTVLHQDWLNGKEYKCKVSNKALPAPLEKTLSKAKGQPREPQVYTLP  360

Sbjct   353  PSREEMTKNQVSLTCLVKGFYPSDLAVEWESNGQPENNYKTTPPVLDSDGSFFLYSKLTV  412
Query   361  PSREEMTKNQVSLTCLVKGFYPSDLAVEWESNGQPENNYKTTPPVLDSDGSFFLYSKLTV  420

Sbjct   413  DKSRWQQGNVFSCSVMHEALHNHYTQKSLSLSPG  446
Query   421  DKSRWQQGNVFSCSVMHEALHNHYTQRSLSLSPG  454
```

FIGURE 4

(A)
```
         1    20    40    60    80    100   120   140   160   180    219
- Sequence WIgG1_LightChain: unnamed protein product
- Alignments, total 1 object shown
```

(B)
```
Sbjct    1    DVLMTQTPLSLPVSLGDQASISCRSSQYIVHSNGNTYLEWYLQKPGQSPKLLIYKVSNRF    60
Query    1    DVLMTQTPLSLPVSLGDQASQSCRSSQYQVHSNGNTYLEWYLQKPGQSPKLLQYKVSNRF    60

Sbjct   61    SGVPDRFSGSGSGTDFTLKISRVEAEDLGVYYCFQGSHVPLTFGAGTKLEIKRADAAPTV   120
Query   61    SGVPDRFSGSG--TDFTLKQSRVEAEDLGVYYCFQGSHVPLTFGAGTKLEQKRADAAPTV   118

Sbjct  121    SIFPPSSEQLTSGGASVVCFLNNFYPKDINVKWKIDGSERQNGVLNSWTDQDSKDSTYSM   180
Query  119    SQFPPSSEQLTSGGASVVCFLNNFYPKDQNVKWKQDGSERQNGVLNSWTDQDSKDSTYSM   178

Sbjct  181    SSTLTLTKDEYERHNSYTCEATHKTSTSPIVKSFNRNEC    219
Query  179    SSTLTLTKDEYERHNSYTCEATHKTSTSPQVKSFNRNEC    217
```

- Sequence WIgG1_HeavyChain: unnamed protein product
- Alignments, total 1 object shown (B)
```
Sbjct    1    QVQLKESGPGLVAPSQSLSITCTVSGFSLLGY------------GVNWVRQPPGQGLEWL   48
Query    1    QVQLKKSGPGLVAPSQSLSITCTVSGFSLLGYNIHWVKCLSLGYGVNWVRQPPGQGLEWL   60

Sbjct    49   MGIWGDGSTDYNSALKSRISITKDNSKSQVFLKMNSLQTDDTAKYYCTRAPYGKQYFAYW  108
Query    61   GNIWGDGSTDYNSALKSRITLSKDNGKSQVFLKMNSLQTDDTAKYYCTRAPYGKQYFAYW  120

Sbjct   109   GQGTLVTVSAAKTTPPSVYPLAPGSAAQTDSMVTLGCLVKGYFPEPVTVTWNSGSLSSGV  168
Query   121   GQGTLVTVSAAKTTPPSVYPLAPGSAAQTNSMVTLGCLVKGYFPEPVTVTWNSGSLSSGV  180

Sbjct   169   HTFPAVLQSDLYTLSSSVTVPSSTWPSETVTCNVAHPASSTKVDKKIVPRDCGCKPCICT  228
Query   181   HTFPAVLQSDLYTLSSSVTVPSSTWPSKTVTCNVAHPASSTKVDKNDVPRDCGCKPCECT  240

Sbjct   229   VPEVSSVFIFPPKPKDVLTITLTPKVTCVVVDISKDDPEVQFSWFVDDVEVHTAHTQPRE  288
Query   241   VPEVSSVFIFPPKPKDVLTITLTPKVTCVVVDSKDDPEVQFSWFVDDVEVHTAKTQPRK  300

Sbjct   289   EQFNSTFRSVSELPIMHQDWLNGKEFKCRVNSAAFPAPIERTISKTRGRPKAPQVYTIPP  348
Query   301   EQFNSTFRSVSELEDMHQDWLNGKEFRCRVNSAAFPAFEKTESKTRGRPKAPQVYTEPP  360

Sbjct   349   PKEQMAKDKVSLTCMITDFFPEDITVEWQWNGQPAENYKNTQPIMDTDGSYFVYSKLNVQ  408
Query   361   PKEQMAKDKVSLTCMETDFFPKDETVENQWNGQPAENYKNTQEDMDTDGSYFVYSKLNVQ  420

Sbjct   409   KSNWEAGNTFTCSVLHEGLHNHHTEKSLSHSPG  441
Query   421   KSNWEAGNTFTCSVLHEGLHNHHTEKSLSHSPG  453
```

METHODS AND SYSTEMS FOR ASSEMBLY OF PROTEIN SEQUENCES

CROSS-REFERENCE TO RELATED APPLICATIONS

This application claims all benefit of including priority from U.S. Provisional Application No. 62/338,279, titled "METHODS AND SYSTEMS FOR ASSEMBLY OF PEPTIDE SEQUENCES" filed on May 18, 2016, which is incorporated herein by reference.

SEQUENCE LISTING

The Sequence Listing is provided as a file entitled 56071034_2US_SEQ.txt created Aug. 9, 2017, Which is 40 Kb in size. The information in the electronic format of the sequence listing is incorporated herein by reference in its entirety.

FIELD

Embodiments relate to the field of protein sequence assembly and, more specifically, to de novo protein sequencing using weighted de Bruijn graphs.

BACKGROUND

Monoclonal antibodies are playing highly successful roles in therapeutic strategies due to their mechanisms of variations [1]. However, it is such variations that have also defied many from an automated system to sequence them. Each monoclonal antibody (mAb) sequence is a novel protein that requires de novo sequencing as the variable regions of the antibody protein has no resembling sequences or proteins in existing databases.

SUMMARY

In accordance with an aspect, there is provided method of determining amino acid sequence of a polypeptide or protein from mass spectrometry data using weighted de Bruijn graph. Purified proteins or polypeptides are cleaved into peptides, and the peptides are subjected to mass spectrometry. A list of peptide sequences is derived from mass spectrometry data by de novo sequencing, and amino acid confidence scores are determined from peak fragment ion intensity. A weighted de Bruijn graph is constructed for the list of peptide sequences having node weights defined by k–1 mer confidence scores. At least one contig is assembled from the de Bruijn graph by connecting nodes with highest k–1 mer confidence scores.

In accordance with another aspect, there is provided computer implemented system for determining amino acid sequence of a polypeptide or protein from mass spectrometry data using weighted de Bruijn graph, the system including one or more processors and non-transitory computer readable media, the computer implemented system comprising a mass spectrometer configured generate a mass spectrometry fragment ion data of peptides cleaved from the polypeptide or protein, and a processor configured to convert mass spectrometry fragment data into a list of peptide sequences and determine amino acid confidence scores. The processor is further configured to perform weighted de Bruijn graph approach for the list of peptide sequences by assigning node weights defined by k–1 mer confidence scores and assembling at least one contig from the de Bruijn graph.

BRIEF DESCRIPTION OF THE FIGURES

Embodiments of the invention may best be understood by referring to the following description and accompanying drawings. In the drawings:

FIG. 2 shows assembly results for the WIgG1 light chain. (A) BLAST alignment of the top assembled contigs from list PSM-DN against the target light chain. (B) Zoom-in details of the alignment in (A), where "Sequence WIgG1 LightChain: unamed protien produced" (SEQ ID NO:1), "seq0×WIgG1 LightChain" (SEQ ID NO:2), "seq1×WIgG1 LightChain" (SEQ ID NO:3), and "seq4×WIgG1 LightChain" (SEQ ID NO:4). (C) BLAST alignment of the full-length contig assembled from list PSM-DD against the target light chain. (D) Details of the alignment in (C), where "Sbjct" (SEQ ID NO:5), and "Query" (SEQ ID NO:6).

FIG. 4 shows assembly results for the HUMAN heavy chain. (A) BLAST alignment of the top assembled contigs from list PSM-DDS against the target heavy chain. (B) BLAST alignment of the template-alignment-based merging of PSM-DDS contigs against the target heavy chain. (C) Details of the alignment in (B), where "Sbjct" (SEQ ID NO:9), and "Query" (SEQ ID NO:10).

FIG. 5 shows assembly results from list PSM-DD with k=6 for the WIgG1 light chain. (A) BLAST alignment of the contig against the target light chain. (B) Details of the alignment in (A), where "Sbjct" (SEQ ID NO:11), and "Query" (SEQ ID NO:12).

FIG. 6 shows assembly results from list PSM-DD for the WIgG1 heavy chain. (A) BLAST alignment of the contig against the target heavy chain. (B) Details of the alignment in (A), where "Sbjct" (SEQ ID NO:13), and "Query" (SEQ ID NO:14).

DETAILED DESCRIPTION

Beginning from the low-throughput sequencing methods using Edman degradation [2], progress has been made in the past decades in relation to sequencing. Especially, liquid chromatography coupled with tandem mass spectrometry (LC-MS/MS) is a useful technology in peptide/protein identification. High throughput sequencing requires computational approaches and computerized approaches for the data processing and analysis, including de novo sequencing directly from tandem mass spectra [3-5] and database search methods that use existing protein sequence databases [6-12]. Despite advances in computer technology, computational approaches pose technical challenges in optimizing an ability to obtain outputs of a sufficient quality while being constrained by available computing resources, such as processing speed, memory, and bandwidth, among others.

For example, various versions of shotgun protein sequencing (SPS) use CID/HCD/ETD [13-19] fragmentation methods and other techniques to increase the coverage, and have achieved significant progress in attempt to fully sequence proteins, especially antibodies. Other methods have assumed the existence of similar proteins [20], a known genome sequence [21], or combined top-down and bottom up approaches [22]. In spite of these efforts, full-length de novo sequencing from tandem mass spectra of proteins with unknown sequences, such as antibodies remains a challenging open problem [16, 17].

Leonhard Euler wondered how he could cross the Pregel River traveling through each of the seven bridges of Konigsberg exactly once. Euler's idea has been widely adopted in the concept of de Bruijn graph, which plays an important role in the problem of sequence assembly [23]. The performance of de Bruijn graph has been demonstrated in genome and transcriptome assemblers such as Velvet [24], Trinity [25], and others. In the field of de novo protein sequencing, the de Bruijn graph has been used for spectral alignment (A-Bruijn) in [18], and has also been extended to top-down mass spectra (T-Bruijn) [19]. However, incomplete peptide fragmentation, missing or low coverage, and ambiguities in spectra interpretation still pose challenges to existing tools to achieve full-length de novo assembly of protein sequences [16].

De novo protein sequencing is desirable spectrometry-based proteomics, especially for novel proteins such as monoclonal antibodies for which there is high variation and genome information is often limited or not available. Proteomics workflow may involve a tight integration of biological and experimental procedures together with computational and statistical steps.

Figure 1:
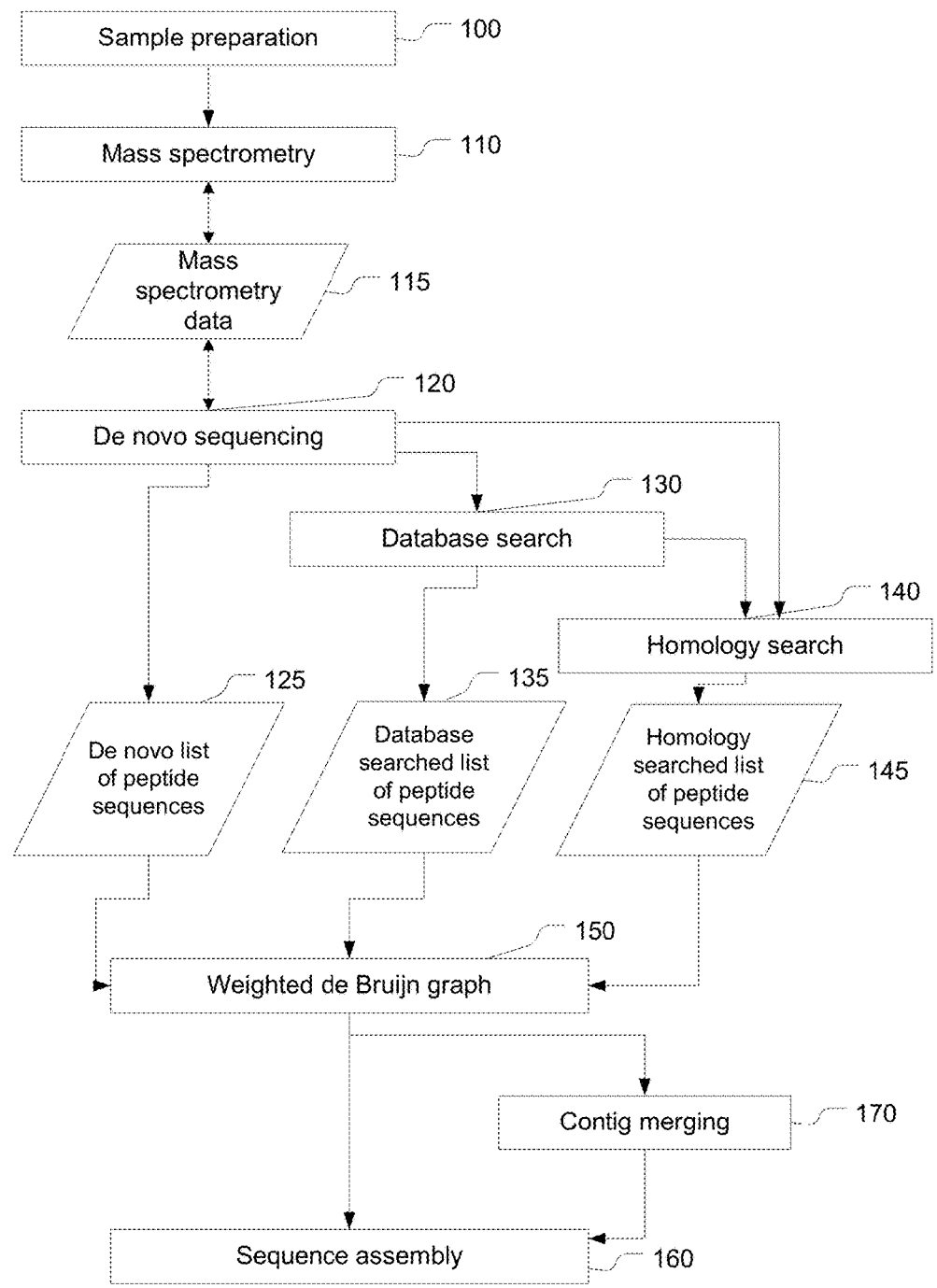
FIG. 1 shows an embodiment workflow of protein sequence determination and assembly using a weighted de Bruijn graph.

Existing strategies to improve the sensitivity and scope of proteomic generally involve large sample quantities and multi-dimensional fractionation, which sacrifices throughput. Alternatively, efforts to improve the sensitivity and throughput of protein quantification limit the number of features that can be monitored. For this reason, proteomics research is typically divided into two categories: discovery and targeted proteomics. Discovery proteomics optimizes protein identification by spending more time and effort per sample and reducing the number of samples analyzed. In contrast, targeted proteomics strategies limit the number of features that will be monitored and then optimize the chromatography, instrument tuning and acquisition methods to achieve the highest sensitivity and throughput for hundreds or thousands of samples. An example workflow of protein sequence determination and assembly is illustrated in FIG. 1.

Figure 9:
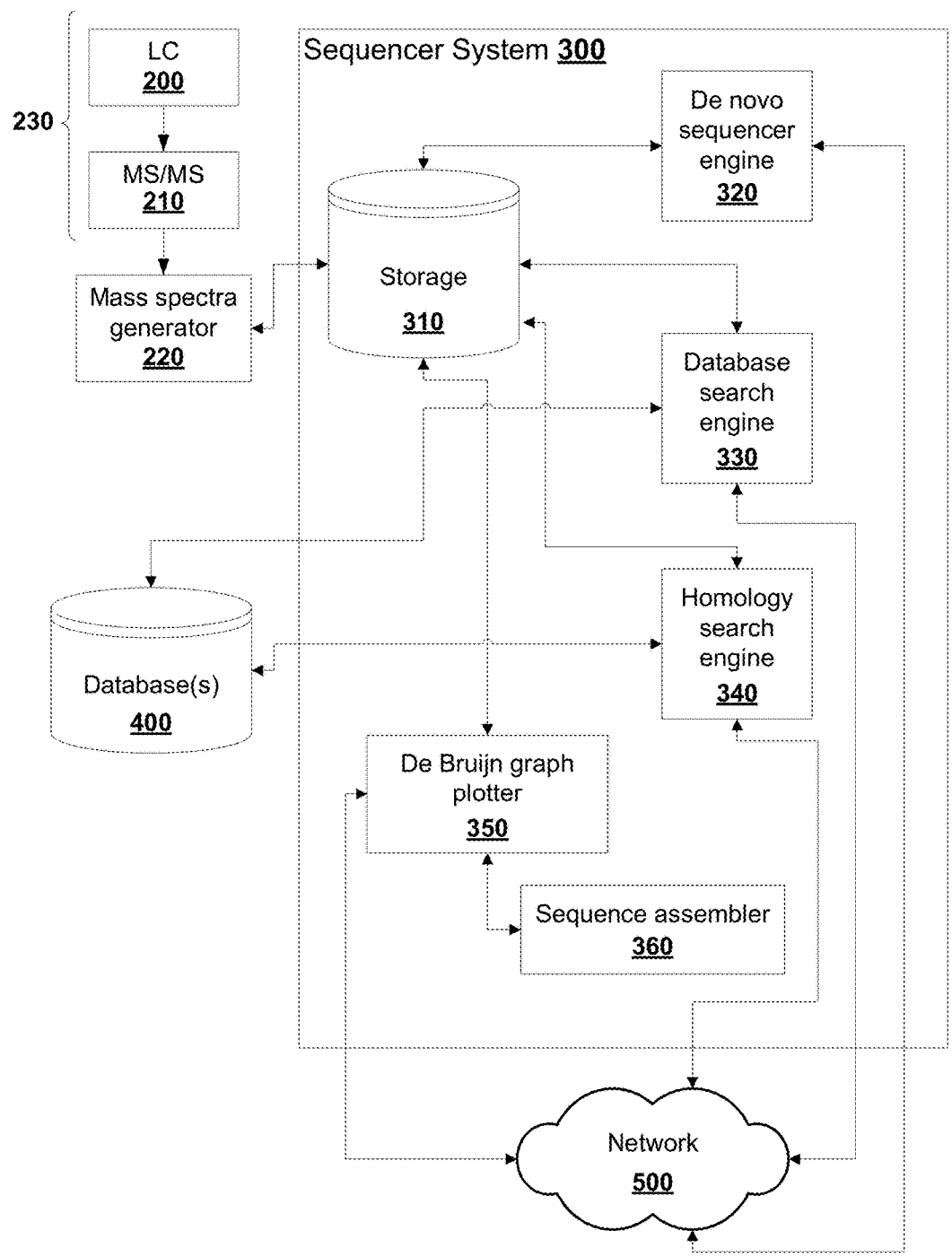
FIG. 9 shows an embodiment of a system comprising a LC-MS/MS and a sequence assembler for determining protein or polypeptide sequence from mass spectrometry data using weighted de Bruijn graph.

An example system hardware configuration for protein sequence determination and assembly is conceptually illustrated in FIG. 9. This example system utilizes liquid chromatography tandem mass spectrometry (LC-MS/MS) (230) which receives a peptide mixture cleaved from a protein of interest and obtains raw mass spectra data.

The system of FIG. 9 is a computer-implemented system where electronic components are controlled and configured to perform protein sequencing. Since proteins are cleaved into peptides first, protein sequencing is a difficult endeavor as peptide sequences require rearrangement and assembly to arrive at the sequence of the original protein. Each peptide sequence consists of one or more amino acids. However, there are many possible permutations in which peptide sequences can be assembled and the original protein may have repeated sequence segments. The system is configured to identify potential arrangements of the peptide sequences that are probabilistically more likely to be the original protein sequence.

Protein sequencing assembly is a difficult computational problem and Applicants have developed specific methods and approaches that aid in assembling full-length monoclonal antibody sequences. Computational techniques described herein are adapted for receiving strings and data sets representative of biological information and data (e.g., strings of genetic sequences) of novel proteins such as monoclonal antibodies for which genome information is often limited or not available.

The system is configured to process these strings and data sets in accordance with specific computational methods and approaches in an attempt to assemble protein (e.g., monoclonal antibody) sequences. An approach according to some embodiments to reassemble the sequences includes translating amino acids sequences (for example, represented by individual characters of a string) into substrings of uniform length, the substrings which are then used to populate a directed graph data structure model, and the directed graph data structure model is then traversed to arrive at potential candidates for sequences that represent the original protein sequence.

Mass spectra generator (220) provides one or more mass spectra data sets provided in one or more interchange formats or standardized formats wherein values of peak intensity and mass are stored ordered pairs of peak readings. These peak readings correspond to physical mass to charge ratio of ions as obtained by the mass spectrometer (210). These data sets may be provided in the form of a container or package whereby a number of individual data sets, together represent the mass spectra reading of peptides of a novel protein. The container may itself include header or metadata information that is indicative of the interrelationships and ordering of the various individual data sets. These data sets are provided to a sequencer system (300), which stores the data sets on data storage (310), which, for example, may include physical storage media hosting databases, flat files, relational databases, among others.

In some embodiments, the LC-MS/MS has an integral command input/output circuitry and system; or in other embodiments, the LC-MS/MS command input/output circuitry is coupled with the sequence analyzer. In some embodiments, a first device control is coupled to the LC-MS/MS and a second control is couple to the sequencer system. Alternatively in some embodiments, a single device control is coupled to both the LC-MS/MS and the sequence analyzer.

The mass spectra data sets are then provided to de novo sequencer engine (320) which is an engine implemented on a processor that is adapted for determining amino acid sequence of a peptide from mass spectrometry data. Confidence information (e.g., in the form of overhead or metadata) is associated with each of the identified amino acids (e.g., errors that may be cause by fragmentation process, ambiguities in mass spectra interpretation, contaminants, imperfect identification techniques, experimental error).

The de novo sequencer engine (320) receives the mass spectra data sets, determines distances between various peaks of the mass spectra data sets, the distance being translated (e.g., through comparison to a hash table or a look up table) to identify a predictive amino acid corresponding to the distance between the peaks. The de novo sequencer engine (320) then predictively transforms the predictive amino acids to generate a peptide sequence.

The database search engine (330) is an additional and optional engine that is configured to receive the peptide sequence and conducts an automated comparison with a reference database library (e.g., an external database) to match peptides against existing known sequences in a reference database (400) to identify errors (e.g., mismatch), e.g., by applying a mask filter to identify whether a mismatch exists between segments of peptide biological sequence data sets.

The homology search engine (340) is an additional and optional engine that can be utilized to predict and identify homologies in relation to the peptides to identify potential equivalent sequences in an attempt to identify potential additional variations of potential peptide sequences. As described herein, conducting homology searches may improve and fine-tune the list of potential peptide sequences.

The De Bruijn graph plotter (350) receives the lists of potential peptide sequences and extracts substrings of consistent length and instantiates a directed graph structure data model having one or more nodes. Each of the one or more nodes is connected to other nodes, and each of these connections is a path having an associated weight.

The nodes, for example, may be stored in the form of linked lists, database objects, etc., and the connections may be provided in the form of pointers to memory address or locations relating to other nodes. The connections can be one to one or many to many. A processor may be able to traverse, from one node to other nodes by way of the connections, the nodes representing overlap regions between two substrings, where the length of the overlap is one less than the length of the substring. Connections are defined based on the orders in which the substring overlap regions appear within a particular string, and the connections are formed of potential predictive next sequences (e.g., each connection represents a possible next string), and weights are associated with each of these connections indicative of the probability leading to the next string. The directed graph represents, for example, a map of possible substrings, and the connection weights are based at least on the geometric mean of individual confidence scores associated with individual amino acids of the overlap substrings that form the data stored at each node. Not all amino acids are weighted the same, and in some embodiments, the amino acid sequence confidence scores on the ends are weighted higher than the amino acid sequence confidence scores on in the middle. Applicants have determined, in some experiments, that applying weights to the ends of the sequences leads to improved accuracy and identification.

De Brujin graph plotter (350) is configured to traverse the directed graph data structure model in assembling an identified protein sequence. In some instances, more than one potential protein sequence may be identified, and further, these potential protein sequences may be incomplete relative to the length of the original protein sequence, and thus may represent ordered but incomplete sections of the original protein sequence, which may then be rearranged or otherwise transformed to arrive at the original protein sequence.

If more than one potential protein sequence is identified, sequence assembler (360) is a logical unit that is configured to receive these intermediate identified protein sequence strings and to computationally identify areas of potential overlap, the areas of potential overlap between the intermediate identified protein sequence strings being used to rearrange (or to remove overlap) the intermediate identified protein sequence strings to arrive at the original protein sequence.

The sequence assembler (360) and/or the de Brujin graph plotter (350) are then configured to generate an output string having characters representative of the potential amino acids that, together, comprise the protein sequence of the novel protein. This output string may, for example, then be provided across network 500 (e.g., a local area network, a wide area network, a point to point communication infrastructure) for provisioning into one or more downstream computing systems. Downstream computing systems, may for example, include biomarker identifiers, medical diagnostics, monoclonal antibody manufacture, drug discovery, cancer treatment, among others.

Sample Preparation

The first step in a proteomic workflow is the preparation of a peptide sample (100). A protein sample is purified to isolate proteins of interest. The purification process may separate protein from non-protein, and also to separate desired protein from all other proteins. Separation steps usually exploit differences in protein size, physico-chemical properties, binding affinity and biological activity. In the case where a protein is comprised of multiple polypeptides, such as monoclonal antibodies, the sample may undergo a separation step to isolate individual polypeptides, such as chain separation to isolate the light and heavy chains of monoclonal antibodies. Various purification procedures are possible and include, but are not limited to, centrifugation, chromatography, liquid-chromatography, electrophoresis, affinity-chromatography, filtration, and denaturing.

In some embodiments, the sample optionally undergo de-glycosylation and reduction of disulfide bonds. In preferred embodiments, the sample proteins are treated with multiple endoproteases into peptides to improve overall coverage of targeted proteins. Proteins are digested to produce a mixture of peptides, which are separated by high-performance liquid chromatography (HPLC) (200) before mass spectrometry (210). Examples of endoproteases include, but are not limited to, pepsin, trypsin, chymotrypsin, elastase, thermolysin, glutamyl endopeptidase, and neprilysin.

Mass Spectrometry

Following preparation of the protein sample, the sample is introduced to a mass spectrometer (110), including for example, tandem mass spectrometer (MS/MS) and liquid chromatography tandem mass spectrometer (LC-MS/MS) (230). LC-MS/MS combines liquid chromatography (200)

to a tandem mass spectrometer (210). an Mass spectrometer (MS) is a analytical technique that ionizes chemical species and sorts the ions based on their mass-to-charge ratio. Mass spectrometry can be applied to pure samples as well as complex mixtures. In an example MS procedure, a sample, which may be solid, liquid, or gas, is ionized, for example by bombarding it with electrons. This causes some of the sample's molecules to break into charged fragments of various sizes and masses. For example, the peptide is fragmented into fragments of 1 amino acid long, 2 amino acids long, 3 amino acids long, and so forth. These ions are then separated according to their mass-to-charge ratio and detected. The detected ions are displayed as a mass spectra of the relative abundance of detected ions as a function of the mass-to-charge ratio. MS is both high-accuracy and high-throughput.

The overall process for mass spectrometry includes a number of steps, specifically the ionization of the peptides, acquisition of a full spectrum (survey scan) and selection of specific precursor ions to be fragmented, fragmentation, and acquisition of MS/MS spectra (product-ion spectra). The data is processed to either quantify the different species and/or determine the peptide amino acid sequence.

Mass spectrometry data (115) is stored in computer memory (310) or remote memory via a network (500), for example, as a mass spectra or a plot of the ion signal as a function of the mass-to-charge ratio, a data table listing ion signal and related mass-to-charge ratio, a data string comprising pairs of ion signal and related mass-to-charge ratio, where values can be stored in corresponding data fields and data instances. In some embodiments, mass spectra is generated using a mass spectra generator (220). The mass spectra data sets may be stored in various data structures for retrieval, transformation, and modification.

De Novo Sequencing

Analysis and conversion of mass spectrometry data into amino acid sequences entails two approaches: database search and de novo sequencing. Database search involves matching the mass spectra data of the unknown peptide a known peptide sequence, and the peptide with the highest matching score is selected. This approach fails to recognize novel peptides since it can only match to existing sequences in the database.

As used herein, "de novo peptide sequencing" (120) refers to a method in which a peptide amino acid sequence is determined from raw mass spectrometry data. De novo sequencing is an assignment of peptide fragment ions from a mass spectrum. Various approaches are known and used for interpretation of mass spectra. Briefly, an amino acid is determined by two fragment ions having a mass difference that corresponds to an amino acid. This mass difference is represented by the distance between the two fragment ion peaks in a mass spectrum, which approximately equals the mass of the amino acid. De novo sequencing approaches apply various forms of dynamic programming approaches to select fragment ions and predict the amino acids. The dynamic programming approaches also take into account the constraint that the predicted amino acid sequence must have similar mass to the given precursor mass. In some embodiments, a de novo sequencer engine (320) executes a de novo sequencing method to generate a list of peptide sequences.

Examples of de novo peptide sequencing algorithms and software include, but are not limited to: CycloBranch™, DeNovoX™, DeNoS™, Lutefisk™, Novor™, PEAKS™, and Supernovo™. Preferably, PEAKS is used for de novo peptide sequencing.

An amino acid confidence score or positional confidence score for each amino acid in a peptide is determined based on, among other factors, fragment ion intensity. These confidence scores may be determined and stored within memory within one or more data structures, and their values may be represented within one or more data fields. For example, PEAKS software also includes determination of amino acid confidence scores. In one embodiment using PEAKS, each amino acid output in a peptide sequence by PEAKS is associated with a confidence score, ranging from 0 to 100, representing the percentage or probability that the amino acid output at a particular location or position in a peptide sequence is correct.

De novo peptide sequencing approaches convert mass spectrometry data into a list of peptide sequences (125), which is stored in computer memory or storage (310) or remote memory via a network (500), as data strings of a sequence of characters, each character encoding a corresponding amino acid. Specific encoding techniques may be utilized to reduce overall memory footprint and usage, potentially improving computational performance given a finite amount of computational resources In some embodiments the data strings are tagged (e.g., metadata or header information is appended to the data strings to enhance the data strings). Alternatively, peptide sequences are stored as data strings, records, linked lists, or tables of amino acid names or single-letter codes. Amino acid confidence scores are stored in computer memory together with peptide sequences, for example, as tags to sequence data strings, or as linked lists or other data structures whereby each amino acid name or single-letter code in a sequence linked to a corresponding confidence score, such that on retrieval, the information is easier to obtain by way of traversing the data structure through the defined linkages.

Integrated Systems

Due to limitations in peptide fragmentation and coverage, contamination with undesired proteins, incomplete purification and sample preparation, as well as ambiguities in spectra interpretation; complete de novo assembly of protein sequences, in particular unknown protein sequences, remains challenging. To address this problem, an integrated system, an embodiment of which is called ALPS, is developed which overcomes de novo peptide sequencing limitations and allows for the automatic assembly of full-length protein sequences, such as monoclonal antibody sequences from tandem mass spectra. Accordingly, the integrated system may reduce the tedious manual work and decrease the turn-around time associated with protein or polypeptide sequencing. In some embodiments, such an integrated system also reduces sample quantities needed for sequencing; reduces or simplifies sample preparation, and also reduces chromatography or mass spectrometry optimization and instrument tuning; increases sequencing accuracy with smaller sample quantity; reduces overall computer processing demands; reduces total computing components needed to complete sequencing; and/or overcomes ambiguities in mass spectrometry data and interpretation.

The system compiles multiple elements of information into a single pipeline to assemble antibody protein sequences. The system integrates de novo sequencing peptides, their intensity and positional confidence scores, and error-correction information from database and homology search into a weighted de Bruijn graph to assemble protein sequences. As described herein, ALPS performance was demonstrated on two example antibody data sets and showed that ALPS is able to assemble complete monoclonal antibody sequences as long as 446 AA, in some cases at 100% coverage, and up to 100% accuracy, for these data sets.

In a separate embodiment, a special purpose machine is configured and provided for use. Such a special purpose machine is configured with a limited range of functions, and is configured especially to provide features in an efficient device that is programmed to perform particular functions, such as the methods and approaches described herein, pursuant to instructions from embedded firmware or software. In this embodiment, the special purpose machine does not provide general computing functions, for example, to streamline processing and improve computational efficiency. For example, a specific device may be provided in the form of an integrated circuit, such as an application-specific integrated circuit.

This application-specific integrated circuit may include programmed gates that are combined together to perform complex functionality as described above, through specific configurations of the gates. These gates may, for example, form a lower level construct having cells and electrical connections between one another. A potential advantage of an application-specific integrated circuit is improved efficiency, reduced propagation delay, and reduced power consumption. An application-specific integrated circuit may also be helpful to meet miniaturization requirements where space and volume of circuitry is a relevant factor.

For example, in an embodiment, a specific sequencing device is provided that is dedicated to performing the methods and approaches described in some embodiments herein, and this specific sequencing device may be a standalone unit that either receives data through a network interface or a data input receiver, is configured to perform the methods and approaches described in some embodiments herein, and provides output in the form of structured data sets. These outputs, for example, may be provided into downstream computing devices.

Database and Homology Searches

Error-correction of peptide sequences is performed by database and homology searches. In database searches (130), a peptide spectrum match is performed to identify a peptide sequence that best matches the given spectrum. Preferably, a peptide spectrum match passing a given threshold will be regarded as a confident interpretation of the spectrum and subsequently used in subsequent de Bruijn graph analysis (150). Peptide sequences having peptide spectrum match below a given threshold is discarded. The database search will generate more accurate peptide sequences from mass spectrometry data because it is able to correct the de novo sequencing errors using protein database entries.

Examples of database search algorithms or software includes, but are not limited to: Byonic™, Greylag™, InsPecT™, Mascot™, MassMatrix™, MassWiz™, MyriMatch™, OMSSA™, PEAKS DB™, Phenyx™, ProteinPilot Software™, Protein Prospector™, RAId™, SEQUEST™, SIMS™, SimTandem™, SQUID™, X!Tandem™, pFind™. Preferably, PEAK DB is used for database search.

Examples of existing protein sequence databases for database search include, but are not limited to: UniProt™, Protein Information Resource™, Swiss-Prot™, PEDANT™, PROSITE™, Database of Interacting Proteins™, Pfam™, PRINTS™, ProDom™, SignalP™ 3.0, SUPERFAMILY™, neXtProt™, NCBI™, BLAST™, Annotation Clearing House™, InterPro™, ProteomeScout™, DisProt™, MobiDB™, and MaxQuant™. Preferably, UniProt and/or SwissProt is used.

In some embodiments, the list of peptide sequences (125) is error-corrected with database searches to generate a second list of peptide sequences. One embodiment of a second list of peptide sequences is a hybrid PSM set, which is a compilation of peptide sequences from the database search and the list of peptide sequences from de novo sequencing In some embodiments, the second list of peptide sequences is generated using the following three criteria.

1) A threshold is applied to a list of peptide sequences. In some embodiments, a threshold is defined using False Discovery Rate (FDR). FDR is a method of conceptualizing the rate of type I errors in null hypothesis testing when conducting multiple comparisons. FDR-controlling procedures are designed to control the expected proportion of "discoveries" (rejected null hypotheses) that are false (incorrect rejections).

In some embodiments, the threshold is 5% FDR, 4% FDR, 3% FDR, 2% FDR, 1% FDR, 0.5% FDR, 0.1% FDR, 0.05% FDR, or 0.01% FDR. In preferred embodiments, the threshold is 1% FDR.

2) Peptide sequences that were mapped in whole or part to contaminant proteins are filtered out.

3) The average amino acid confidence scores for a given peptide sequence is higher than 10, higher than 20, higher than 30, higher than 40, higher than 50, higher than 60, higher than 70, higher than 80, higher than 90. In preferred embodiments, the average amino acid confidence is higher than 50.

Other additional criteria and constraints may also be used in database searches. A second list of peptide sequences generated using database searches and peptide sequences from de novo sequencing has all amino acid confidence scores assigned as 55, 60, 65, 70, 75, 80, 85, 90, 95. In preferred embodiments, all amino acid confidence scores for the database searched peptide sequences are assigned as 85.

Database searched list of peptide sequences (135) are stored in computer memory or storage (310) or remote memory via a network (500), as data strings of a sequence of characters, each character encoding a corresponding amino acid. In some embodiments the data strings are tagged. Alternatively, peptide sequences are stored as data strings, records, linked lists, or tables of amino acid names or single-letter codes. Amino acid confidence scores are stored in computer memory together with peptide sequences, for example, as tags to sequence data strings, or as linked lists with each amino acid name or single-letter code in a sequence linked to a corresponding confidence score. In some embodiments, a database search engine (330) communicates with existing protein sequence databases (400) and executes a database search approach or method to generate a databased searched list of peptide sequences (135).

In homology searches (140), to detect amino acid variants, a predicted list of peptide sequences are generated by performing a homology search (145) on the list of peptide sequences derived from de novo sequences (125) and/or a database searched list of peptide sequences (135), against existing databases. In one embodiment, a homology search approach attempts to match de novo sequence tags with the database proteins and reconstructs a true sequence to minimize the sum of de novo errors and homology mutations between the true sequence and the one recorded in the database when a significant similarity is found. As used herein, "de novo sequence tags" are subsequences in the de novo sequencing result whose confidence score is consecutively greater than certain threshold, for example, a subsequence having an overall amino acid confidence score higher than that of the de novo peptide sequence from which the subsequence is derived.

Examples of homology search algorithms or software includes, but are not limited to: MS-Homology™ and SPIDER™. Preferably, SPIDER is used for homology search, which may be integrated in the PEAKS software.

Examples of existing protein sequence databases for homology search include, but are not limited to: UniProt™, Protein Information Resource™, Swiss-Prot™, PEDANT™, PROSITE™, Database of Interacting Proteins™, Pfam™, PRINTS™, ProDom™, SignalP™ 3.0, SUPERFAMILY™, neXtProt™, NCBI™, BLAST™, Annotation Clearing House™, InterPro™, ProteomeScout™, DisProt™, MobiDB™, and MaxQuant™. Preferably, UniProt and/or SwissProt is used.

Various criteria is applied to homology searches. In one embodiment, a threshold is applied to a list of peptide sequences. In some embodiments, the threshold is 5% FDR, 4% FDR, 3% FDR, 2% FDR, 1% FDR, 0.5% FDR, 0.1% FDR, 0.05% FDR, or 0.01% FDR. In preferred embodiments, the threshold is 1% FDR.

In one embodiment, peptide sequences that were mapped in whole or part to contaminant proteins are filtered out.

In one embodiment, the average amino acid confidence scores for a given peptide sequence is higher than 10, higher than 20, higher than 30, higher than 40, higher than 50, higher than 60, higher than 70, higher than 80, higher than 90. In preferred embodiments, the average amino acid confidence is higher than 50.

Other additional criteria and constraints may also be used in homology searches. A third list of peptide sequences is generated using homology searches of peptide sequences from de novo sequencing and/or from database searches. This third list of peptide sequences has all amino acid confidence scores assigned as 55, 60, 65, 70, 75, 80, 85, 90, 95. In preferred embodiments, all amino acid confidence scores for the homology searched peptide sequences are assigned as 85.

Homology searched list of peptide sequences (145) are stored in computer memory or storage (310), or remote memory via a network (500), as data strings of a sequence of characters, each character encoding a corresponding amino acid. In some embodiments the data strings are tagged. Alternatively, peptide sequences are stored as data strings, records, linked lists, or tables of amino acid names or single-letter codes. Amino acid confidence scores are stored in computer memory together with peptide sequences, for example, as tags to sequence data strings, or as linked lists with each amino acid name or single-letter code in a sequence linked to a corresponding confidence score. In some embodiments, a homology search engine (340) communicates with existing protein sequence databases (400) and executes a homology search to generate a homology searched list of peptide sequences (145).

The above three lists of peptide sequences are then used in de Bruijn graph analysis to determine the complete sequence of the protein or polypeptide of interest. In one embodiment, only the first list of peptide sequences from de novo sequencing is used for Bruijn graph analysis, or only one of the three lists are used. In another one embodiment, the first and second lists of peptide sequences are used. In yet another embodiment, the first, second, and third lists of peptide sequences are all used. In alternative embodiments, the second and third list of peptide sequences are used.

Weighted De Bruijn Graph Approach

In one embodiment, weighted de Bruijn graph approaches (150) are performed using a list of peptide sequences. In another embodiment, weighted de Bruijn graph techniques are performed in relation to processing multiple lists of peptide sequences, where a weighted de Bruijn graph is mapped for each list of peptide sequences. In some embodiments, the best graph is selected for use in assembling a complete sequence of the protein or polypeptide of interest.

As used herein, "de Bruijn graph" refers to a method of assembling sequences by splitting sequence reads into smaller units or substrings (k-mer) of k-amino acid length. In one embodiment, k is between 3 and 10. In another embodiment, k is between 5 and 10. In yet another embodiment, k is between 5 and 8. In a preferred embodiment, k is 6 or 7. An adjacent k-mer is identified having overlapping sequence by a length of k−1 (k−1 mer).

For example, given a peptide sequence stored as a data string of sequence of characters encoding for amino acids, an example k-mer where k=7, the corresponding k−1 mers are shown below.

| Peptide: | PEACDEFGPPEADKTR |
|---|---|
| k-mer: | CDEFGPP |
| Left k-1 mer: | CDEFGP |
| Left adjacent k-mer: | A<u>CDEFGP</u> |
| Right k-1 mer: | DEFGPP |
| Right adjacent k-mer: | <u>DEFGPP</u>E |

For the above example: Peptide (SEQ ID NO:17); k-mer (SEQ ID NO:18), Left k−1 mer (SEQ ID NO:19), Left adjacent k-mer (SEQ ID NO:20), Right k−1 mer (SEQ ID NO:21), and Right adjacent k-mer (SEQ ID NO:22).

The k value should be large enough to retain enough characteristics of the genome to allow reconstruction, yet are short enough to provide detailed statistics on the pieces for error correction. Overlap between k-mers can be identified, for example, with a mask using bitwise operations. In one embodiment, overlap is identified by masking to amino acid names or amino acid single-letter codes. In other embodiments, overlap is identified by image masks. In yet another embodiment, overlap is identified using hash tables.

A directed graph is then generated by connecting pairs of k−1 mers, with the k−1 mers being the nodes and their connectivity represented by paths between nodes, as shown in the representation below (left: SEQ ID NO:23; right: SEQ ID NO:24.

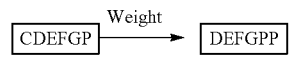

The direction of arrow goes from the left k−1 mer to the right k−1 mer. Therefore, various k−1 mers are connected based on whether they belong to the same k-mer. This connectivity or nodes and paths data structure is represented as a map or a graph. Accordingly, the de Bruijn graph is a directional graph representation or a map of this connectivity. This nodes and paths data structure is stored in computer memory or storage (310), or remote memory via a network (500), as, for example, visual map or graphical representation, or a linked list of nodes. In some embodiments, a de Bruijn graph plotter (340) graphically plots the nodes and paths. The nodes and paths, for example, can be stored in the form of a linked data structure, such as a tree having specified linkages between child and parent nodes, etc. Linkages can be provided in the form of pointers (e.g., memory block address locations), and weights may be stored in the node objects. These linked data structures are configured for ease of traversal and processing.

Where multiple possible connectivity is present for a node, this is represented by a junction with multiple possible paths corresponding to the multiple possible connectivity. Each junction and possible paths may be represented through corresponding linkages in the data structure. To assign a weight on a node, a k−1 confidence score is determined and assigned as the node weight or the weight of the k−1 mer.

In one embodiment, the confidence score of a k−1 mer is defined as the geometric mean of the amino acid confidence scores of the amino acids comprising the k−1 mer. For example, for the left k−1 mer in the example above, the product of the individual 6 amino acid confidence scores associated with the 6 amino acids C, D, E, F, G, P is taken, and then the sixth root of that product is taken.

In some embodiments, the left-most and right-most amino acids of the k−1-mer (C and P in the above example) play more important roles than those in the middle. Hence in these embodiments, instead of standard geometric mean, a weighted geometric mean is used to add more weights to the amino acids at the two ends of the k−1-mer.

In a preferred embodiment, a k−1 confidence score is determined according to Equation I below:

$$\text{score}(k-1mer) = \sum_{\text{peptides containing } k-1mer} \text{intensity(peptide)} \times \left( \prod_{aa \text{ in } k-1mer} (\text{score}(aa))^{\text{weight}(aa)} \right)^{\frac{1}{\sum_{aa \text{ in } k-1mer} \text{weight}(aa)}} \quad (1)$$

wherein score(k−1 mer) is the k−1 mer confidence score; wherein intensity(peptide) is the logarithm of precursor intensity for a peptide based on the mass spectrometry fragment ion data; wherein "aa" is amino acid; wherein score(aa) is the amino acid confidence score; wherein weight (aa) is a weight ratio between amino acids at both ends of the k−1 mer and amino acids at middle positions of the k−1 mer. Example ratios for weight(aa) include, but are not limited to: 3 for amino acids at the end, and 1 for amino acids in the middle; or 7 for amino acids at the end, and 1 for amino acids in the middle. In preferred embodiments, weight(aa) is 5 for amino acids at both ends of the k−1 mer, and 1 for amino acids at middle positions of the k−1 mer.

Equation 1 takes a weighted geometric mean of the amino acid confidence scores of the amino acids comprising the k−1 mer, where amino acids at the two ends of the k−1-mer is given a higher weight than the middle amino acids of the k−1 mer by assigning a larger weight ratio to the confidence scores of the amino acids at the two ends. This weighted geometric mean is multiplied by the sum of fragment ion intensities of the peptides containing the k−1 mer.

Sequence Assembly

Once a de Bruijn graph is constructed a complete sequence of the protein or polypeptide of interest is assembled into a complete protein or polypeptide sequence (160) by connecting all nodes using paths having the highest k−1 mer confidence score at each junction. Identification of a set of linear paths connecting all the nodes is accomplished, for example, using a greedy approach which is a paradigm that follows the problem solving heuristic of making the locally optimal choice at each stage with the hope of finding a global optimum. Examples of greedy approaches include, but are not limited to: greedy walks approaches, pure greedy approaches, orthogonal greedy approaches, and relaxed greedy approaches.

Preferably, greedy walks is used. In some embodiments, a sequence assembler (360) is used to execute a greedy approach.

Ideally, one contig is assembled from the weighted de Bruijn graph by connecting all the nodes. A "contig" is an assembled sequence from overlapping sequence segments, from which the complete sequence may be deduced. As used herein, the term "contig" refers to a sequence of amino acids that is assembled from the de Bruijn graph.

A contig is are stored in computer memory or storage (310), or remote memory via a network (500), as data strings of a sequence of characters, each character encoding a corresponding amino acid. In some embodiments the data strings are tagged. Alternatively, peptide sequences are stored as data strings, records, linked lists, or tables of amino acid names or single-letter codes.

In some embodiments, the weighted de Bruijn graphs may only yield multiple contigs since not all the nodes can be connected in one continuous linear set of paths. In such cases, the contigs are merged (170) to determine a full sequence of the polypeptide or protein of interest. The contigs may be merged, through the use of an alignment approach. For example, template alignment, local alignments, or multiple sequence alignments can be used. Preferably, template alignment is used.

Where multiple weighted de Bruijn graphs are generated for multiple lists of peptide sequences, the resulting best contig or set of contigs are used for sequence assembly.

Monoclonal Antibody Sequencing

The systems and methods described herein are useful in sequencing monoclonal antibodies. Monoclonal antibodies are used in a variety of applications, including, diagnostic test for detecting presence of target substances, analytic and chemical uses to purity target compounds from mixtures (ie. immunoprecipitation), and therapeutic treatments such as cancer treatment by blocking target molecule functions or by modulating signaling pathways. The specific binding affinity to the same epitope of an antigen allows for specific binding of target molecules or antigens, while the high variability of the variable region allows for the design and manufacture of various different monoclonal antibodies to various different targets. However, it is also this mechanism of variation that poses many challenges. Small changes in the variable region alters the binding specificity of the antibody, hence highly accurate sequencing is needed to characterize antibodies. As well, the high variability has deterred the development of an automated system to sequence antibody proteins and polypeptide, since each monoclonal antibody sequence is a novel protein whose sequence cannot be determined by simply matching against existing databases. Hence, an integrated system such as ALPS, allows for both accuracy and streamlined protein sequencing of novel proteins.

The following examples are illustrative of various aspects of the invention, and do not limit the broad aspects of the invention as disclosed herein.

EXAMPLES

Methods
Sample Preparation
SDS-PAGE

The heavy and light chains of an antibody were separated by SDS polyacrylamide gel electrophoresis (SDS-PAGE). Briefly, 0.5 μg of the antibody was placed, reduced, and denatured in gel loading buffer. The sample was subsequently loaded into three wells that contained a 10% precast gel (BioRad). The gel was subjected to 180 constant volts for 50 minutes. Following this, the gel was stained with Coomassie Blue. Gel bands that contained the antibody were excised.

Deglycosylation and Endoprotease Digestion

Each excised band was reduced with dithiothreitol (DTT). Free cysteine residues were then alkylated using iodoacetamide. The heavy chain bands were deglycosylated with PNGase F (Roche Diagnostics) overnight using the manufacturer's protocol. The pH was adjusted for each protease and three enzyme digestions were carried out overnight according to the manufacturer's (Roche) instructions: 1) Asp N, 2) Chymotrypsin, 3) Trypsin. The peptides were extracted from the gel bands, desalted using C18 Zip-Tip® (Millipore) and dried in a speed-vac.

LC-MS/MS

The desalted peptides were suspended in 0.1% formic acid and 1/10 of each of the digests were subjected to LC-MS/MS on a Thermo-Fisher Scientific Q-Exactive (Q-E) Orbitrap mass spectrometer. The gradient was supplied using a Thermo-Fisher EASY nLC-1000 UHPLC system and consisted of 0 to 40% acetonitrile in 0.1% formic acid over 1 hour at 250 nL per minute. The Q-E was run in a data dependent mode with 10 MS/MS events per cycle. The parent ion resolution was 70,000 FWHM and the fragment ion resolution was 17,500 FWHM. The 12 resulting raw data files (6 for each antibody, 3 for the light chain and 3 for the heavy chain) were used.

Data Processing and Cleaning

The raw data were first imported into PEAKS Studio 7.5, preprocessed (precursor mass correction, MS/MS de-isotoping and deconvolution, peptide feature detection), and three lists of peptides were generated for subsequent assembling.

PSM-DN: Results from De Novo Sequencing

This is the first stage of de novo sequencing from tandem mass spectra. PEAKS de novo sequencing was performed with precursor and fragment error tolerance as 10 ppm and 0.02 Da, respectively. Carbamidomethylation (Cys) was set as a fixed modification and oxidation (Met) and deamidation (Asn/Gln) as variable modifications. At most three variable modifications per peptide were allowed. The peptide sequences identified by de novo sequencing were exported along with their feature areas and positional confidence scores.

PSM-DD: Results from De Novo Sequencing and PEAKS DB

PEAKS DB [6], the database search module in PEAKS Studio 7.5, was then used in the second stage to identify peptide spectrum matches (PSMs) from existing protein databases. To determine a confidence threshold for PSMs, the PEAKS-embedded target-decoy approach, "decoy fusion" [6], was used to estimate the false discovery rate (FDR) of the PEAKS DB result. In the experiments, it was assumed the species of the samples were unknown. Therefore, the data sets were searched first against the UniProt database [26] to identify the species. Once the species was confirmed, a second database search was performed on the data sets against the in-house antibody database assembled for the identified species. Note that the antibody database used in the PEAKS DB search also includes 329 commonly observed contaminant proteins. This contaminant database contains proteins from the cRAP contaminant database [27], the MaxQuant contaminant database [28], and a few contaminants used in ABRF iPRG 2012 study. More specifically, the WIgG1 data sets were searched against the mouse antibody database and the HUMAN IgG1 data sets were searched against the human antibody database in these experiments. Other search parameters were kept the same as used in the respective de novo sequencing. Based on the current database search results and the de novo sequencing results from the previous stage, a hybrid PSM set was generated for the subsequent antibody sequencing assembling according to three criteria: 1) the scores of the PSMs identified by PEAKS DB must be higher than a specified threshold (in this case, which was selected with FDR 1.0%); 2) the PSMs that were mapped to contaminant proteins must be filtered out; and 3) the Average Local Confidence (ALC) scores of PSMs identified from PEAKS de novo sequencing must be higher than 50 and the peptide sequence cannot be mapped a contaminant protein with more than seven amino acid residues. Each PSM in the hybrid set was also accompanied by its feature area and positional confidence scores for the subsequent assembling. The motivation of using such a hybrid PSM set was to take advantage of database information to resolve amino acid assignment ambiguities of de novo sequencing peptides.

PSM-DDS: Results from De Novo Sequencing and PEAKS DB and SPIDER

Biological samples for antibody sequencing commonly contain proteins with slightly different sequences to the ones recorded in the existing protein databases. In some cases, ignoring those mutated peptides can lead to errors in the assembled complete antibody sequencing reducing accuracy. To detect amino acid variants, the data sets were searched by the SPIDER [29], integrated in PEAKS software, against the given antibody database. SPIDER tries to match the de novo sequence tags with the database proteins and reconstructs a true sequence to minimize the sum of de novo errors and homology mutations between the true sequence and the one recorded in the database when a significant similarity is found. The PSMs reported by SPIDER are then filtered at 1.0% FDR. Similarly to the aforementioned hybrid PSM set in the previous stage, a PSM set containing PSMs from PEAKS de novo sequencing, PEAKS DB, and SPIDER were exported for the subsequent assembling.

Weighted de Bruijn Graph Construction and Contigs Assembly

The three lists of peptides together with their intensities (feature areas) and positional confidence scores were obtained from PEAKS as described in the previous procedures. Subsequently, all possible k-mers were extracted from the peptides. Each k-mer was further split into two overlapping substrings of length $k-1$, called left and right $(k-1)$-mers. The left and right $(k-1)$-mers represent nodes in the de Bruijn graph while the k-mer corresponds to a directed edge in the graph, pointing from the left to the right $(k-1)$-mer. Experimental results suggest that $k=6$ or $k=7$ are optimal for the assembly of antibody sequences. Using shorter k-mers will encounter the issue of repetitiveness in target sequences, while using longer k-mers will not have enough peptides coverage for the assembly task.

The peptides' intensities and positional confidence scores provide more useful information and substantially improve the assembly quality from the de Bruijn graph. In particular, the confidence score of each $(k-1)$-mer was defined as the weighted geometric mean of its amino acids' confidence scores. The weight of each $(k-1)$-mer was then calculated as the product of its confidence score and the intensity of the peptide from which the $(k-1)$-mer was extracted. Since a $(k-1)$-mer can appear in multiple peptides, its weight was accumulated over the processing of all those peptides. Formulation of the node weights is defined in the following equation:

$$\text{score}(k-1mer) = \sum_{\text{peptides containing } k-1mer} \text{intensity(peptide)} \times \left(\prod_{aa \text{ in } k-1mer} (\text{score}(aa))^{weight(aa)}\right)^{\frac{1}{\sum_{aa \text{ in } k-1mer} weight(aa)}} \quad (1)$$

After the de Bruijn graph was constructed, contigs were assembled by performing greedy walks through the graph as following:

Step 1: select the (k–1)-mer with the highest weight as the seed for the new contig.

Step 2: extend the seed using a seed and extend alignment approach in both forward and backward directions by selecting the neighbors with the highest weights and concatenating the new amino acids to the current contig. This step was repeated until no further extension was possible. Starting with one node as the starting seed, the assembled sequence is extended by extending the starting seed in both directions one node at a time. After a (k–1)-mer had been used for seed or extension, it was discarded from graph.

Step 3: repeat steps 1 and 2 until the graph became empty or a desired number of contigs had been generated.

The assembly output was a list of contigs in the order that they were extracted from the graph. In addition, each contig was accompanied by positional confidence scores for its residues.

Final Protein Sequence

If the de Bruijn assembler produced a few contigs rather than a single full-length one to cover the target sequence, the contigs were combined into the final sequence by using a template alignment. A template sequence that is most closely matched to the contigs was obtained from the database. Subsequently, the contigs were aligned to the template sequence to determine their relative positions to each other. Finally, the contigs were merged to one single sequence and their overlapping regions were resolved by using the corresponding positional confidence scores.

Results

Antibody samples were first prepared according to the procedure described in Methods. Raw LC-MS/MS data were then imported into PEAKS Studio 7.5 for preprocessing (precursor mass correction, MS/MS de-isotoping and deconvolution, peptide feature detection). Subsequently, three following lists of peptides were generated for the assembly task. The first peptides list, PSM-DN, was generated from PEAKS de novo sequencing with precursor and fragment error tolerance as 10 ppm and 0.02 Da, respectively. Carbamidomethylation (Cys) was set as a fixed modification and oxidation (Met) and deamidation (Asn/Gln) as variable modifications. At most three variable modifications per peptide were allowed.

Next, PEAKS DB was used to identify peptide spectrum matches (PSMs) from existing protein databases. First, the data sets were searched against the UniProt database [26] to identify the species and then a second search was performed against the in-house antibody database assembled for the identified species. Based on the current database search results and the de novo sequencing results from the first stage, a hybrid PSM set was generated as the second peptides list, PSM-DD, according to three criteria: 1) the scores of the PSMs identified by PEAKS DB must be higher than a specified threshold (which was selected with a false discovery rate (FDR) 1.0%); 2) the PSMs that were mapped to contaminant proteins must be filtered out; and 3) the Average Local Confidence (ALC) scores of PSMs identified from PEAKS de novo sequencing must be higher than 50 and the peptide sequence cannot be mapped a contaminant protein with more than seven amino acid residues. The motivation of using such a hybrid PSM set was to take advantage of database information to resolve amino acid assignment ambiguities of de novo sequencing peptides.

To take into account potential mutations in de novo sequencing peptides, the data sets were searched against the corresponding antibody database by using PEAKS SPIDER [29]. SPIDER tries to match de novo sequence tags with the database proteins and reconstructs a true sequence to minimize the sum of de novo errors and homology mutations between the true sequence and the one recorded in the database when a significant similarity is found. Finally, a hybrid PSM set containing PSMs from PEAKS de novo sequencing, PEAKS DB, and SPIDER were generated as the third peptides list, PSM-DDS. More details of the database search parameters can be found in Methods.

Three lists of peptides, PSM-DN, PSM-DD, and PSM-DDS were then imported into the de Bruijn graph assembler. In addition to the peptide sequences, peptides confidence scores and peptides intensities (feature areas) were also incorporated to form a weighted de Bruijn graph (Equation (1), Methods). The experiments showed that those weight information played a crucial role to select the right paths for contigs extension and substantially improve the assembly quality.

De novo assembly results for two datasets of monoclonal antibody sequences are presented herein, each including a light chain and a heavy chain, hence a total of four samples. The first dataset, WIgG1, was generated from the LC-MS/MS of the Intact mAb Mass Check Standard purchased from Waters. It is an intact mouse antibody purified by Protein-A with known molecular weights and amino acid sequences of both the light and heavy chains. The molecular weight and the target sequences can be readily used for the evaluation of pipeline performance. The other dataset, HUMAN (IgG1) was generated from purified human antibody sample. The purified antibody sample has no amino acid sequences provided when purchased from SIGMA-Aldrich. To evaluate the pipeline, the amino acid sequences were manually worked out from the LC-MS/MS data with the assistance of PEAKS 7.5. The coverage and accuracy of both two target sequences were 100% guaranteed by the validation with three strict criteria: 1) The false discovery rate (FDR) at the peptide spectrum match (PSM) level was less than 0.1%; 2) Each amino acid was supported by at least 20 PSMs; 3) Each amino acid was supported by a pair of its fragmental ion peaks with at least 5% relative intensity.

The light chain lengths are in the range of 211-219 AA, while the heavy chains of IgGs are much longer, around 450 AA, and hence more challenging for the assembly task. For each sample, three lists of peptides PSM-DN, PSM-DD, and PSM-DDS were prepared, as described earlier, and then performed the assembly on each list. To evaluate the assembly results, BLAST alignments of assembled contigs were performed against the corresponding target sequences and then measured the coverage and accuracy.

Assembly Results for Dataset WIgG1

Figure 2:
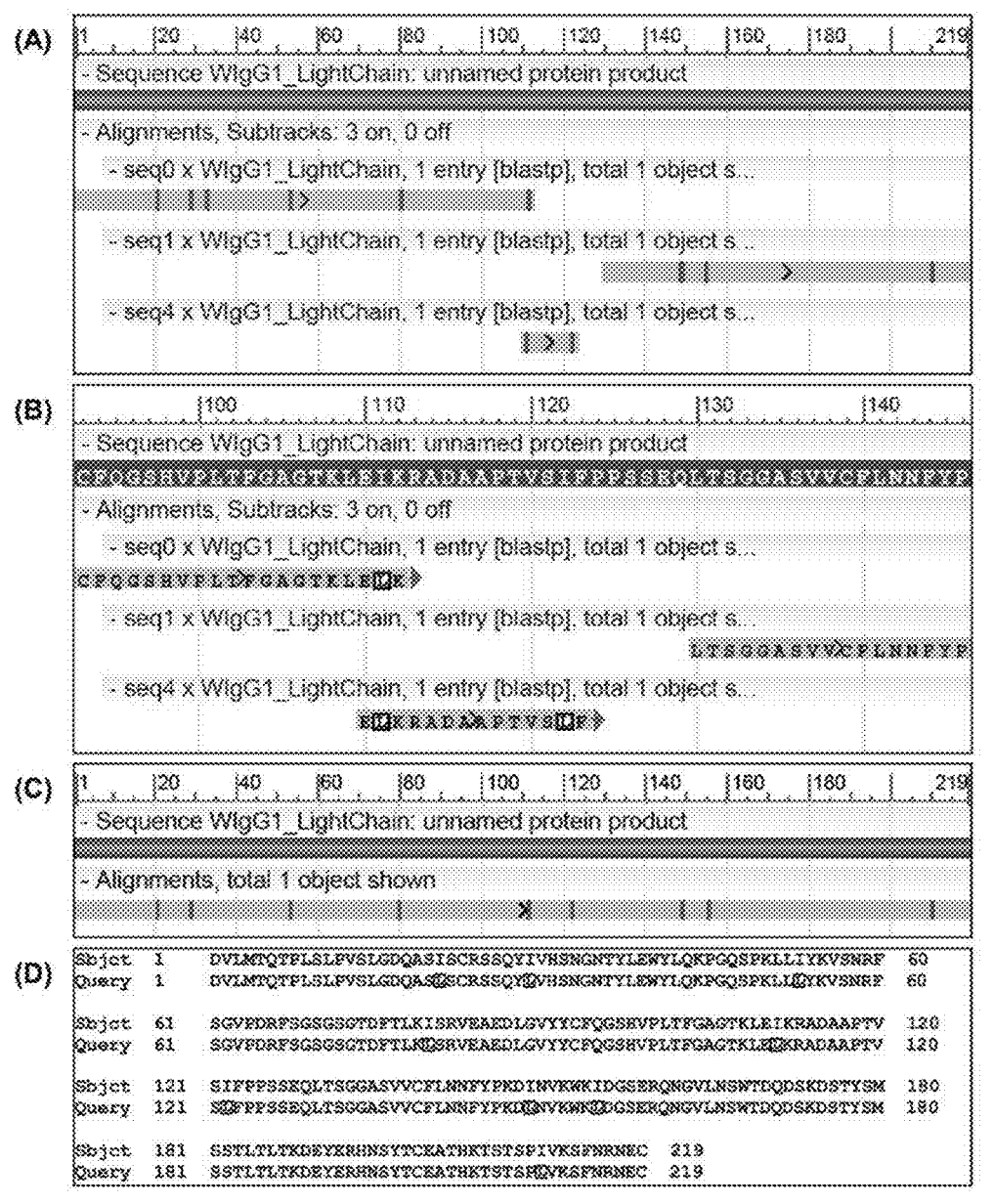

The light chain of the WIgG1 dataset has 219 AA. The de Bruijn assembly result from list PSM-DN with k=6 is summarized in the BLAST alignment in FIG. 2, part (A). The first two contigs seq0 and seq1 retrieved from the de Bruijn assembler, with lengths 109 and 93 respectively, together covered 202 AA of the target light chain. The 17-AA gap between them is covered by some other lower-ranking contigs (for simplicity, only seq4 is shown in FIG. 2, part (A)). Missing or low signal-to-noise of de novo peptides in that region posed challenges for de Bruijn graph and producing such gaps. In particular, FIG. 2, part (B) shows the detailed alignment at that 17-AA gap. Seq0 could not be further extended to the right due to the missing of the 5-mer "LELKR" in list PSM-DN. On the other hand, seq1 was wrongly extended to the left after the 5-mer "LTSGG" due to an error of de novo spectra interpretation where "EQ" was wrongly interpreted as "DAA" in several de novo peptides.

Such limitations of de novo peptides can be handled by incorporating information from the database and homology search and using hybrid PSMs as described earlier. Indeed, from both lists PSM-DD and PSM-DDS, the de Bruijn assembler with k=7 was able to retrieve the full-length contig of the WIgG1 light chain. FIG. 2, part (C) shows the BLAST alignment of the assembled contig against the target sequence with 100% coverage and nine mismatches. The alignment details in FIG. 2, part (D) further show that all nine mismatches are I-to-L amino acids which have the same mass. Thus, the assembled contig also achieved 100% accuracy. For k=6, the de Bruijn assembler made a wrong branching and hence caused a 2-AA deletion in the output contig (FIG. 5).

Figure 3:
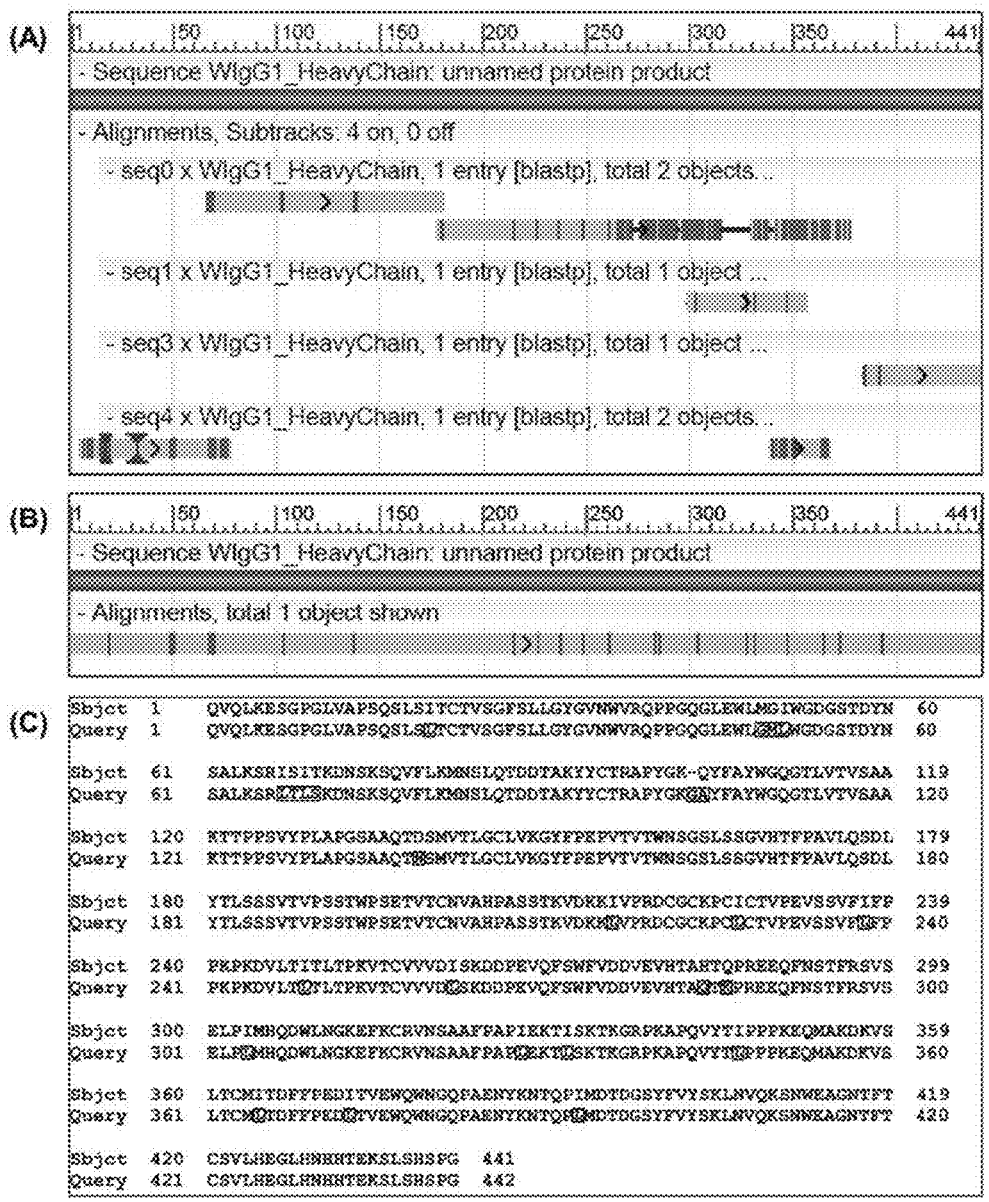
FIG. 3 shows assembly results for the WIgG1 heavy chain. (A) BLAST alignment of the top assembled contigs from list PSM-DN against the target heavy chain. (B) BLAST alignment of the full-length contig assembled from list PSM-DDS against the target heavy chain. (C) Details of the alignment in (B), where "Sbjct" (SEQ ID NO:7), and "Query" (SEQ ID NO:8).
Figure 7A:
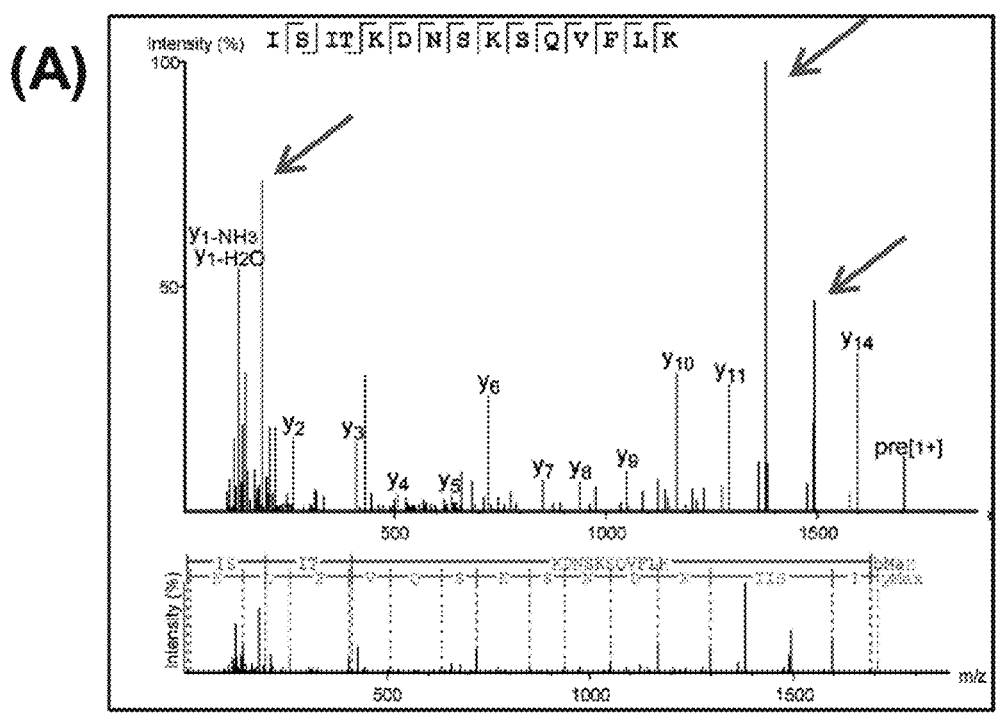
FIG. 7A shows a high-confidence spectra to support corrections of the WIgG1 heavy chain, where (A) assignment of residues "ISIT" at positions 67-70 in the WIgG1 heavy chain did not match three peaks in the spectrum.
Figure 7B:
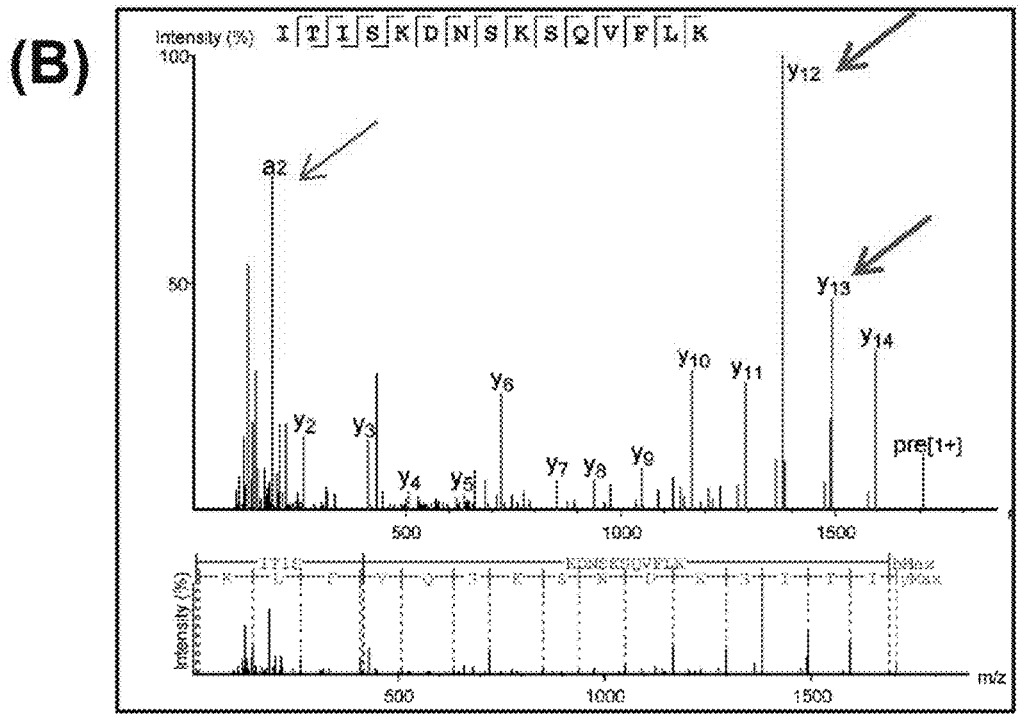
FIG. 7B shows a high-confidence spectra to support corrections of the WIgG1 heavy chain, where (B) the spectrum is better interpreted with the assignment "ITIS" as in the assembly result.
Figure 7C:
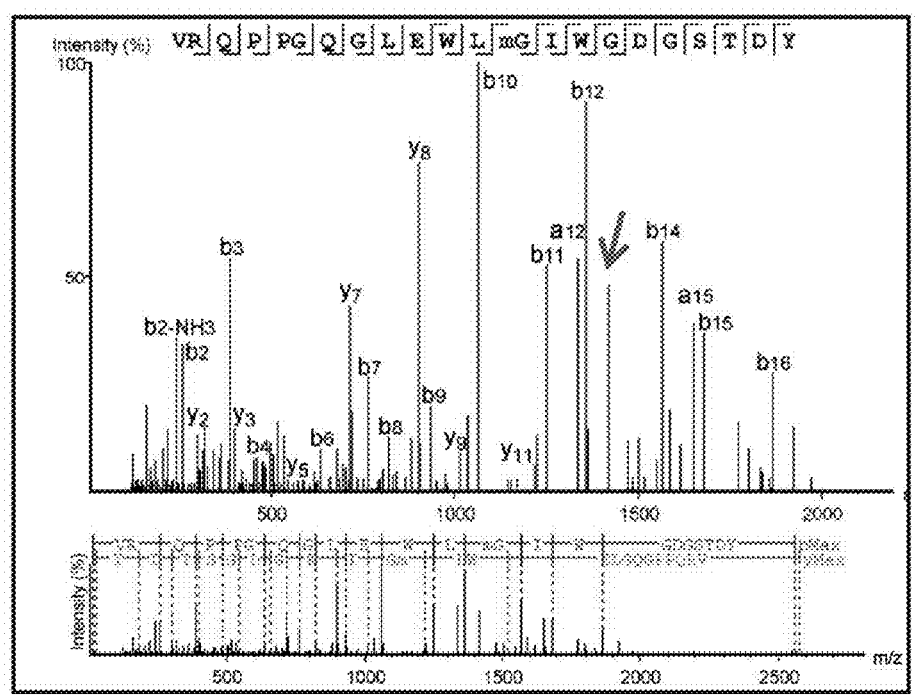
FIG. 7C shows a high-confidence spectra to support corrections of the WIgG1 heavy chain, where (C) assignment of residues "MG" at positions 49-50 in the WIgG1 heavy chain did not match one peak in the spectrum.
Figure 7D:
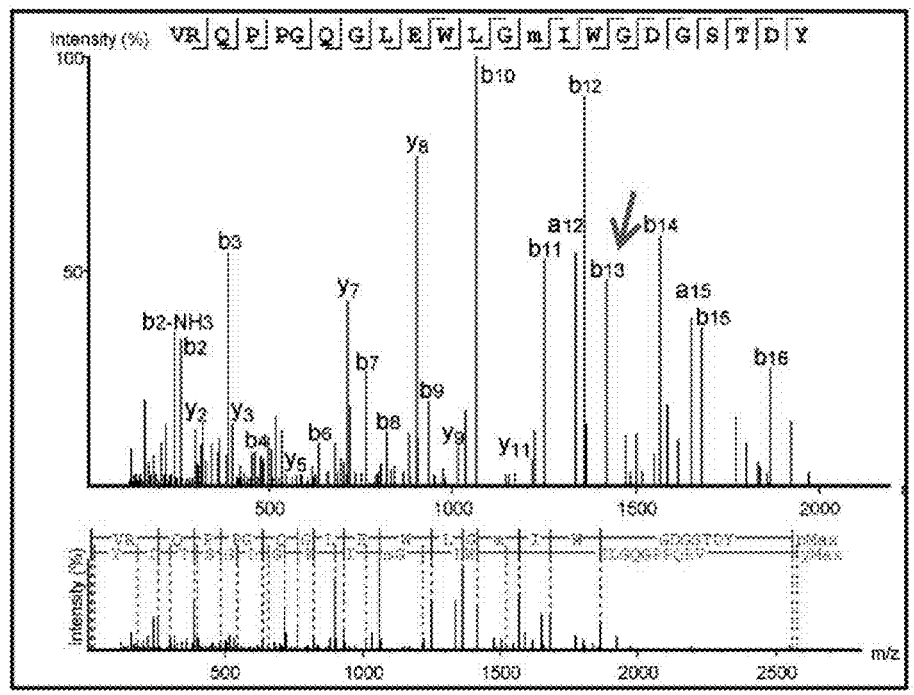
FIG. 7D shows a high-confidence spectra to support corrections of the WIgG1 heavy chain, where (D) The spectrum is better interpreted with the assignment "GM".

The WIgG1 heavy chain is 441-AA long, more than twice the light chain, and hence is more difficult for the assembly task. In FIG. 3, part (A), a few top contigs from the de Bruijn assembly result from list PSM-DN is reported. The longest contig was 219-AA and covered two segments of total length 194 AA, that is, 43.99% of the target sequence. Other contigs also provided additional coverage. However, as can be seen from FIG. 3, part (A), the problems of missing coverage and fragmentation can be complicated such as in the case of this heavy chain than for the light chain which may not be easily solved by simply using de novo peptides alone. Hence, additional information from the database and homology search may be included. Surprisingly, the de Bruijn assembler was able to assemble a 442-AA contig from list PSM-DDS that fully covered the target heavy chain (FIG. 3, part (B)).

The alignment details in FIG. 3, part (C) further show that the assembled contig from list PSM-DDS has one single insertion and twenty-four mismatches. Sixteen mismatches are I-to-L amino acids with the same mass. The consecutive insertion and mismatch at position 103 corresponds to one error of de novo spectra interpretation Q-to-GA. The error resulted in an assembled contig having an accuracy of 98.19% (433/441). However, there is strong evidence to believe that the target sequence provided by Waters has errors at positions 49-50, 68, 70 and the assembled contig indeed gives the correct amino acids at those positions. Further details are illustrated in FIGS. 7A-7D. Hence, the accuracy of the assembled contig for the WIgG1 heavy chain is 99.09% (437/441).

The result from list PSM-DD, however, is slightly less accurate with a 12-AA insertion as the de Bruijn assembler made a wrong branching due to low signal-to-noise (see FIG. 6). The result can be improved with, for example, further optimized sample preparation and mass spectrometry optimization.

Assembly Results for Dataset HUMAN

Figure 8:
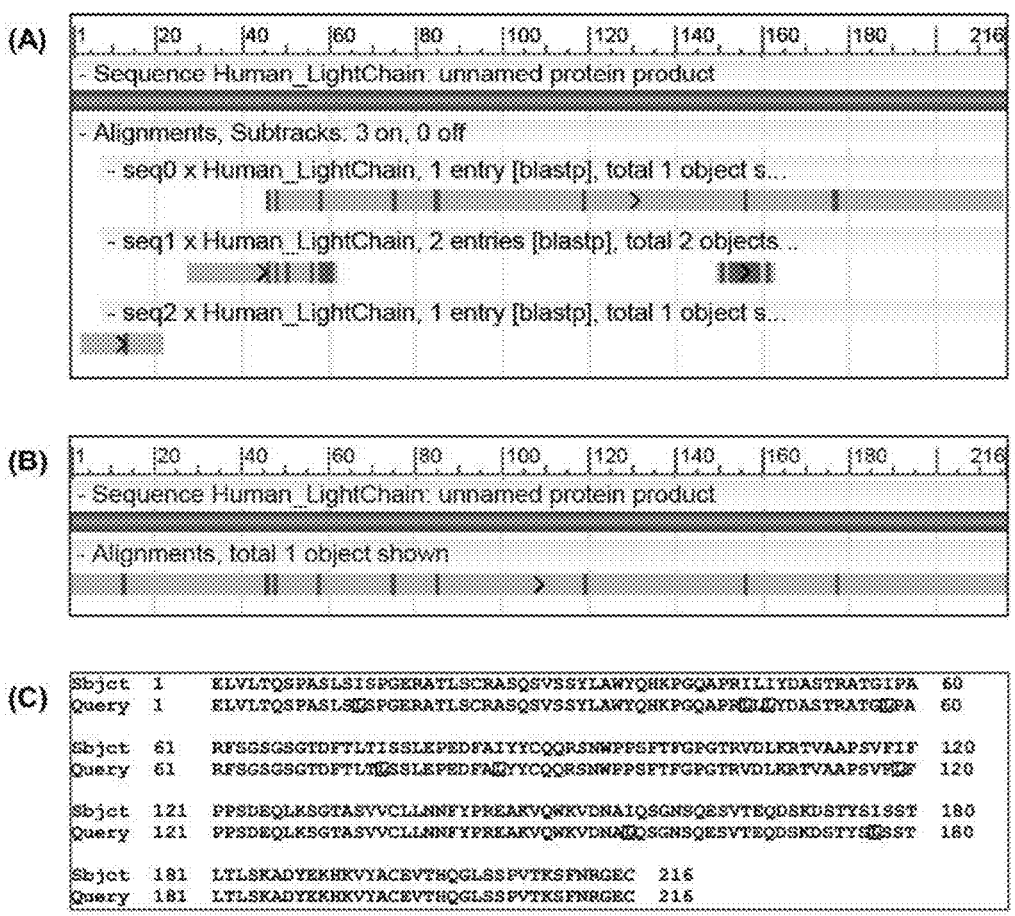
FIG. 8 shows assembly results for the HUMAN light chain. (A) BLAST alignment of the top assembled contigs from list PSM-DN against the target light chain. (B) BLAST alignment of the fulllength contig assembled from list PSM- DD against the target light chain. (C) Details of the alignment in (B), where "Sbjct" (SEQ ID NO:15), and "Query" (SEQ ID NO:16).

For the HUMAN light chain of length 216 AA, the de Bruijn assembler again was able to obtain the full-length contig from the two lists PSM-DD and PSM-DDS at 100% accuracy. If only de novo peptides in list PSM-DN were used, the longest contig in the de Bruijn assembly result was 175-AA long, covering 170 AA (78.70%) of the target light chain (FIG. 8).

The HUMAN heavy chain is 446-AA long and was the most difficult among four sequences for the assembly task. The best de Bruijn assembly result was obtained from list PSM-DDS and included three contigs of length 346, 92, 67, which together fully covered the target heavy chain (FIG. 4, part (A)). Even additional information from the database and homology search was not enough for the de Bruijn assembler to resolve the problems of missing coverage and low signal-to-noise of peptides and to produce a single full-length contig. Hence, the contigs were further combined to be retrieved from the de Bruijn graph by aligning them to a template protein sequence from the database that is most closely matched to those contigs. Based on that alignment and the positional confidence scores of the contigs, they were merged into the final sequence of length 454 AA. As shown in FIGS. 4B and 4C, the assembled sequence has 9 mismatches two of which are I-to-L amino acids. The assembled sequence also has a 8-AA insertion at position 102. Hence, the accuracy of the assembled sequence is 96.64% (431/446) for the HUMAN heavy chain. Missing peptides coverage, even in the database and homology search pose challenges for complete sequencing.

Discussion

De novo assembly of novel protein sequences is one of the most challenging problems in mass spectrometry-based proteomics. The main difficulties of assembly task include limitations in peptides fragmentation and coverage, as well as ambiguities in spectra interpretation. An integrated system ALPS combines de novo sequencing peptides, fragment ion intensities and positional confidence scores, and error-correction information from database and homology search into a weighted de Bruijn graph to assemble protein sequences.

The ALPS evaluation on two antibody data sets are provided herein, each including a light chain and a heavy chain. Table 1 summarizes the obtained three full-length contigs from the de Bruijn assembler for three of the four antibody sequences. The assembled contigs for the two light chains (with lengths 219 and 216 AA, respectively) achieved 100% accuracy, while the contig for the WIgG1 heavy chain (length 441AA) achieved 99.09% accuracy. For the remaining HUMAN heavy chain (length 446AA), three contigs of lengths 346, 92, 67 were obtained, which together fully covered that heavy chain. The final sequence combined from those three contigs achieved 96.64% accuracy. In addition, Table 2 summarizes that the de novo assembly results were substantially improved by integrating the information from database and homology search together with de novo peptides and their positional confidence scores.

The ALPS system addresses the problem of automated and complete de novo assembly of monoclonal antibody sequences. Furthermore, ALPS can be further generalized for complete de novo assembly of many novel proteins with appropriate databases and experiments setting.

Although preferred embodiments of the invention have been described herein, it will be understood by those skilled in the art that variations may be made thereto without departing from the spirit of the invention or the scope of the appended claims. All documents disclosed herein, including those in the following reference list, are incorporated by reference.

TABLE 1

Summary of ALPS De Novo Assembly Results. The target sequence coverage was calculated as the percentage of amino acids of the target sequence that were covered by the contigs. The target sequence accuracy was calculated as the percentage of matched amino acids. I-to-L were not considered as mismatched.

|  | WIgG1 - Light (219aa) | WIgG1 - Heavy (441aa) | Human - Light (216aa) | Human - Heavy (446aa) |
|---|---|---|---|---|
| Assembly Results | Full-length contig from de Bruijn assembler | Full-length contig from de Bruijn assembler | Full-length contig from de Bruijn assembler | 3 contigs (lengths 346, 92, 67) from de Bruijn assembler; Complete sequence merged from 3 contigs |
| Target Sequence Coverage (%) | 100.00 | 100.00 | 100.00 | 100 |
| Target Sequence Accuracy (%) | 100.00 | 99.09 | 100.00 | 96.64 |

TABLE 2

Length (AA), Number of Amino Acids Recovered (AA), Target Sequence Coverage (%), and Contig Assembly Accuracy (%) of the Longest Contigs. The target sequence coverage was calculated as the percentage of amino acids of the target sequence that were covered by the contig. The contig assembly accuracy was calculated as the percentage of amino acids of the contig that were aligned to the target sequence.

|  | WIgG1 - Light (219aa) | WIgG1 - Heavy (441aa) | Human - Light (216aa) | Human - Heavy (446aa) |
|---|---|---|---|---|
| PSM-DN with frequencies | 114; 109; 49.77; 95.61 | 143; 129; 29.25; 90.21 | 175; 170; 78.70; 97.14 | 98; 74; 16.59; 75.51 |
| PSM-DN with weights | 109; 109; 49.77; 100.00 | 219; 194; 43.99; 88.58 | 175; 170; 78.70; 97.14 | 154; 121; 27.13; 78.57 |
| PSM-DD with weights | 219; 219; 100.00; 100.00 | 453; 441; 100.00; 97.35 | 216; 216; 100.00; 100.00 | 346; 344; 77.13; 99.42 |
| PSM-DDS | 219; 219; 100.00; 100.00 | 442; 441; 100.00; 99.77 | 216; 216; 100.00; 100.00 | 346; 344; 77.13; 99.42 |

REFERENCES

1. Maggon, K. Monoclonal antibody "gold rush", Curr. Med. Chem. 14, 1978-1987 (2007).
2. Pham, V., Henzel, W. J., Arnott, D., Hymowitz, S. et al. De novo proteomic sequencing of a monoclonal antibody raised against OX40 ligand. Anal. Biochem. 352, 77-86 (2006).
3. Ma, B., Zhang, K., Hendrie, C., Liang, C. et al. PEAKS: Powerful Software for Peptide De Novo Sequencing by Tandem Mass Spectrometry. Rapid Commun. Mass Spectrom. 17(20), 2337-2342 (2003).
4. Chi, H., Sun, R. X., Yang, B., Song, C. Q. et al. pNovo: De novo peptide sequencing and identification using HCD Spectra. J. Proteome Res, 9(5), 2713-2724 (2010).
5. Frank, A. & Pevzner, P. PepNovo: de novo peptide sequencing via probabilistic network modeling. Anal. Chem. 77(4), 964-973 (2005).
6. Zhang, J., Xin, L., Shan, B., Chen, W. et al. PEAKS DB: De Novo Sequencing Assisted Database Search for Sensitive and Accurate Peptide Identification. Mol. Cell. Proteomics 10.1074/mcp. M111.010587 (2011).
7. Eng, J. K., McCormack, A. L. & Yates, J. R. An approach to correlate tandem mass spectral data of peptides with amino acid sequences in a protein database. J. Am. Soc. Mass Spectrom. 5(11), 976-989 (1994).
8. Cottrell, J. S. & London, U. Probability-based protein identification by searching sequence databases using mass spectrometry data. Electrophoresis 20(18), 3551-3567 (1999).
9. Geer, L. Y., Markey S. P., Kowalak, J. A. Wagner, L. et al. Open mass spectrometry search algorithm. J. Proteome Res. 3(5), 958-964 (2004).
10. Craig, R. & Beavis, R. C. TANDEM: matching proteins with tandem mass spectra. Bioinformatics 20(9), 1466-7 (2004).
11. Cox, J., Nauhauser, N., Michalski, A., Scheltema, R. A. et al. Andromeda: a peptide search engine integrated into the MaxQuant environment. J. Proteome Res. 10(4), 1794-1805 (2011).
12. Xu, T., Venable, J. D., Park, S. K., Cociorva, D. et al. ProLuCID, a fast and sensitive tandem mass spectra-based protein identification program. in Molecular & cellular proteomics 5, S174-S174 (2006)
13. Bandeira, N., Tang, H., Bafna, V. & Pevzner, P. Shotgun protein sequencing by tandem mass spectra assembly. Anal. Chem. 76, 7221-7233 (2004).
14. Bandeira, N., Tsur, D., Frank, A. & Pevzner, P. A. Protein identification by spectral networks analysis. Proc. Natl. Acad. Sci. USA 104, 6140-6145 (2007).
15. Bandeira, N., Pham, V., Pevzner, P., Arnott, D. & Lill, J. R. Automated de novo protein sequencing of monoclonal antibodies. Nat. Biotechnol. 26, 1336-1338 (2008).
16. Guthals, A., Clauser, K. R., Frank, A. M., & Banderira, N. Sequencing-grade de novo analysis of MS/MS triplets (CID/HCD/ETD) from overlapping peptides. J. Proteome Res. 12, 2846-2857 (2013).
17. Guthals, A., Clauser, K. R. & Bandeira, N. Shotgun protein sequencing with meta-contig assembly. Mol. Cell. Proteomics, 11(10), 1084-96 (2012).
18. Bandeira, N., Clauser, K. R. & Pevzner, P. A. Shotgun protein sequencing: assembly of peptide tandem mass spectra from mixtures of modified proteins. Mol. Cell. Proteomics, 6(7), 1123-1134 (2007).
19. Vyatkina K., Wu S., Dekker L. J., VanDuijn M. M. et al. De Novo Sequencing of Peptides from Top-Down Tandem Mass Spectra. J. Proteome Res. 14(11), 4450-62, (2015)
20. Liu, X., Han, Y., Yuen, D. & Ma, B. Automated protein (re)sequencing with MS/MS and a homologous database yields almost full coverage and accuracy. Bioinformatics, 25(17), 2174-2180 (2009).
21. Castellana, N. E., Pham, V., Arnott, D., Jill, J. R. & Bafna, V. Template proteogenomics: sequencing whole proteins using an imperfect database. Mol. Cell. Proteomics, 9(6), 1260-1270 (2010).
22. Liu, X., Dekker, L., Wu, S., Vanduijin, M. M. et al. De novo protein sequencing by combining top-down and bottom-up tandem mass spectra. J. Proteome Res., 13(7), 3241-3248 (2014).
23. Compeau, P. E., Pevzner, P. A. & Tesler, G. How to apply de Bruijn graphs to genome assembly. Nat. Biotechnol. 29, 987-991 (2011).

24. Zerbino, D. R. & Birney, E. Velvet: Algorithms for de novo short read assembly using de Bruijn graphs. Genome Res. 18(5), 821-9, (2008).
25. Grabherr, M. G., Haas, B. J., Yassour, M., Levin, J. Z. et al. Full-length transcriptome assembly from RNA-Seq data without a reference genome. Nat. Biotechnol. 29, 644-652 (2011).
26. Uniprot swiss-prot. http://www.uniprot.org/uniprot/.
27. The common Repository of Adventitious Proteins, cRAP. ftp://ftp.thegpm.org/fasta/cRAP.
28. MaxQuant Contaminant Database. http://maxquant.org/contaminant.zip
29. Han, Y., Ma, B. & Zhang, K. SPIDER: Software for Protein Identification from Sequence Tags Containing De Novo Sequencing Error. J. Bioinform. Comput. Biol. 3(3), 697-716 (2005).

The invention claimed is:

1. A computer implemented system for determining amino acid sequence of a polypeptide from mass spectrometry data using weighted de Bruijn graph, the system including one or more processors and non-transitory computer readable media, the computer implemented system comprising:

a mass spectrometer configured to generate a mass spectrometry fragment ion data of peptides cleaved from the polypeptide; and a processor configured to:

a) convert the fragment ion data into a first list of peptide sequences, wherein the peptide sequences are sequence reads of the mass spectrometry fragment ions;

b) determine an amino acid confidence score for each amino acid in the peptide sequences, wherein the amino acid confidence score is determined based on a corresponding fragment ion intensity from the mass spectrometry fragment ion data and represents a probability that an amino acid at a position in a peptide sequence is correct;

c) construct a first weighted de Bruijn graph for the first list of peptide sequences by:

identifying a k-amino acid length substring (k-mer) from the first list of peptide sequences;

identifying an adjacent k-amino acid length substring, having overlapping sequence (k−1 mer) by a length of k−1; and generating a map of all possible k−1 mers by assigning each k−1 mer as a node and representing relationships between each k−1 mer as paths connecting the nodes, wherein nodes having multiple possible relationships are represented by junctions with multiple paths; and assigning each path a k−1 mer confidence score determined according to Equation I:

$$\text{score}(k-1mer) = \sum_{\text{peptides containing } k-1mer} \text{intensity}(\text{peptide}) \times \left( \prod_{aa \text{ in } k-1mer} (\text{score}(aa))^{weight(aa)} \right)^{\frac{1}{\sum_{aa \text{ in } k-1mer} weight(aa)}} \quad (1)$$

wherein score(k−1 mer) is the k−1 mer confidence score;

wherein intensity(peptide) is the logarithm of precursor intensity for a peptide based on the mass spectrometry fragment ion data;

wherein aa is amino acid;

wherein score(aa) is the amino acid confidence score;

wherein weight(aa) is a weight ratio, where amino acids at both ends of the k−1 mer have a higher weight than amino acids at middle positions of the k−1 mer; and d) assemble at least one contig from the first weighted de Bruijn graph by connecting all nodes using paths having the highest k−1 mer confidence score at each junction.

2. The computer implemented system of claim 1, wherein k is between 5 and 10.

3. The computer implemented system of claim 2, wherein k is 6 or 7.

4. The computer implemented system of claim 1, wherein weight(aa) is 5 for amino acids at both ends of the k−1 mer, and 1 for amino acids at middle positions of the k−1 mer.

5. The computer implemented system of claim 1, wherein one contig is assembled from the weighted de Bruijn graph and the one contig represents a full amino acid sequence of the polypeptide.

6. The computer implemented system of claim 1, wherein multiple contigs are assembled from the weighted de Bruijn graph and are merged into a full amino acid sequence of the polypeptide.

7. The computer implemented system of claim 1, wherein the mass spectrometer is tandem mass spectrometer (MS/MS) or liquid chromatography tandem mass spectrometer (LC-MS/MS).

8. The computer implemented system of claim 1, wherein the fragment data is converted into the first list of peptide sequences by de novo sequencing using PEAKS™.

9. The computer implemented system of claim 1, wherein the a processor configured to further configured to:
generate a second list of peptide sequences by:
matching the first list of peptide sequences against candidate peptides searched from an existing sequence database, wherein the candidate peptide has a threshold of 1% False Discovery Rate (FDR);
correcting errors in the first list of peptide sequences based on a best match candidate peptide; and
assigning all amino acid confidence score as 85; and
generate a second weighted Bruijn graph or the third list of peptide sequences.

10. The computer implemented system of claim 9, wherein the second list of peptide sequences is generated by PEAKS DB™.

11. The computer implemented system of claim 9, wherein the a processor configured to further configured to:
generate a third list of peptide sequences by:
performing a homology search for homologous peptides using the first and second list of peptide sequences, wherein the homologous peptide has a threshold of 1% FDR;
predicting peptide sequences based on the homology search; and
assigning all amino acid confidence score as 85; and
generate a third weighted Bruijn graph for the third list of peptide sequences.

12. The computer implemented system of claim 11, wherein the third list of peptide sequences is generated by PEAKS™ and SPIDER™.

13. The computer implemented system of claim 9, wherein the most complete at least one contig from the first or the second weighted Bruijn graph is used to assemble a full amino acid sequence of the polypeptide.

14. The computer implemented system of claim 11, wherein the most complete at least one contig from the first, second, or third weighted Bruijn graph is used to assemble a full amino acid sequence of the polypeptide.

15. The computer implemented system of claim 1, wherein the polypeptide is an antibody protein.

16. A method of determining amino acid sequence of a polypeptide from mass spectrometry data by constructing a weighted de Bruijn graph, the method comprising:
a) purifying the polypeptide and cleaving the polypeptide into peptides
b) analyzing the peptides through mass spectrometry;
c) obtaining mass spectrometry fragment ion data of the peptides and converting the fragment ion data into a first list of peptide sequences, wherein the peptide sequences are sequence reads of the mass spectrometry fragment ions;
d) determining an amino acid confidence score for each amino acid in the peptide sequences, wherein the amino acid confidence score is determined based on a corresponding fragment ion intensity from the mass spectrometry fragment ion data and represents a probability that an amino acid at a position in a peptide sequence is correct;
e) constructing a first weighted de Bruijn graph for the first list of peptide sequences by:
identifying a k-amino acid length substring (k-mer) from the first list of peptide sequences;
identifying an adjacent k-amino acid length substring, having overlapping sequence by a length of k−1 (k−1 mer); and
generating a map of all possible k−1 mers by assigning each k−1 mer as a node and representing relationships between each k−1 mer as paths connecting the nodes, wherein nodes having multiple possible relationships are represented by junctions with multiple paths; and
assigning each path a k−1 mer confidence score determined according to Equation I:

$$\text{score}(k-1mer) = \sum_{\text{peptides containing } k-1mer} \text{intensity(peptide)} \times \left( \prod_{aa \text{ in } k-1mer} (\text{score}(aa))^{weight(aa)} \right)^{\frac{1}{\sum_{aa \text{ in } k-1mer} weight(aa)}} \quad (1)$$

wherein score(k−1 mer) is the k−1 mer confidence score;
wherein intensity(peptide) is the logarithm of precursor intensity for a peptide based on the mass spectrometry fragment ion data;
wherein aa is amino acid;
wherein score(aa) is the amino acid confidence score;
wherein weight(aa) is a weight ratio, where amino acids at both ends of the k−1 mer have a higher weight than amino acids at middle positions of the k−1 mer; and
f) assembling at least one contig from the first weighted de Bruijn graph by connecting all nodes using paths having the highest k−1 mer confidence score at each junction.

17. The method of claim 16, wherein k is between 5 and 10.

18. The method of claim 17, wherein k is 6 or 7.

19. The method of claim 16, wherein weight(aa) is 5 for amino acids at both ends of the k−1 mer, and 1 for amino acids at middle positions of the k−1 mer.

20. The method of claim 16, wherein one contig is assembled from the weighted de Bruijn graph and the one contig represents a full amino acid sequence of the polypeptide.

21. The method of claim 16, wherein multiple contigs are assembled from the weighted de Bruijn graph and are merged into a full amino acid sequence of the polypeptide.

22. The method of claim 16, wherein the mass spectrometry is tandem mass spectrometry (MS/MS) or liquid chromatography tandem mass spectrometry (LC-MS/MS).

23. The method of claim 16, wherein the fragment data is converted into the first list of peptide sequences by de novo sequencing.

24. The method of claim 23, wherein PEAKS™ is used to convert the fragment data into the first list of peptide sequences.

25. The method of claim 16, further comprising:
generating a second list of peptide sequences by:
matching the first list of peptide sequences against candidate peptides searched from an existing sequence database, wherein the candidate peptide has a threshold of 1% False Discovery Rate (FDR);
correcting errors in the first list of peptide sequences based on a best match candidate peptide; and
assigning all amino acid confidence score as 85; and
generating a second weighted Bruijn graph or the third list of peptide sequences.

26. The method of claim 25, wherein the second list of peptide sequences is generated by PEAKS DB™.

27. The method of claim 25, further comprising
generating a third list of peptide sequences by:
performing a homology search for homologous peptides using the first and second list of peptide sequences, wherein the homologous peptide has a threshold of 1% FDR;
predicting peptide sequences based on the homology search; and
assigning all amino acid confidence score as 85; and
generating a third weighted Bruijn graph for the third list of peptide sequences.

28. The method of claim 27, wherein the third list of peptide sequences is generated by PEAKS™ and SPIDER™.

29. The method of claim 25, wherein the most complete at least one contig from the first or the second weighted Bruijn graph is used to assemble a full amino acid sequence of the polypeptide.

30. The method of claim 27, wherein the most complete at least one contig from the first, second, or third weighted Bruijn graph is used to assemble a full amino acid sequence of the polypeptide.

31. The method of claim 16, wherein the polypeptide is an antibody protein.

* * * * *

SEQUENCE LISTING

```
<160> NUMBER OF SEQ ID NOS: 24

<210> SEQ ID NO 1
<211> LENGTH: 54
<212> TYPE: PRT
<213> ORGANISM: Artificial Sequence
<220> FEATURE:
<223> OTHER INFORMATION: unnamed protein product

<400> SEQUENCE: 1

Cys Phe Gln Gly Ser His Val Pro Leu Thr Phe Gly Ala Gly Thr Lys
1               5                   10                  15

Leu Glu Ile Lys Arg Ala Asp Ala Ala Pro Thr Val Ser Ile Phe Pro
            20                  25                  30

Pro Ser Ser Glu Gln Leu Thr Ser Gly Gly Ala Ser Val Val Cys Phe
        35                  40                  45

Leu Asn Asn Phe Tyr Pro
    50

<210> SEQ ID NO 2
<211> LENGTH: 20
<212> TYPE: PRT
<213> ORGANISM: Artificial Sequence
<220> FEATURE:
<223> OTHER INFORMATION: unnamed protein product

<400> SEQUENCE: 2

Cys Phe Gln Gly Ser His Val Pro Leu Thr Phe Gly Ala Gly Thr Lys
1               5                   10                  15

Leu Glu Leu Lys
            20

<210> SEQ ID NO 3
<211> LENGTH: 17
<212> TYPE: PRT
<213> ORGANISM: Artificial Sequence
<220> FEATURE:
<223> OTHER INFORMATION: unnamed protein product

<400> SEQUENCE: 3

Leu Thr Ser Gly Gly Ala Ser Val Val Cys Phe Leu Asn Asn Phe Tyr
1               5                   10                  15

Pro

<210> SEQ ID NO 4
<211> LENGTH: 14
<212> TYPE: PRT
<213> ORGANISM: Artificial Sequence
<220> FEATURE:
<223> OTHER INFORMATION: unnamed protein product

<400> SEQUENCE: 4

Glu Leu Lys Arg Ala Asp Ala Ala Pro Thr Val Ser Leu Phe
1               5                   10
```

-continued

```
<210> SEQ ID NO 5
<211> LENGTH: 219
<212> TYPE: PRT
<213> ORGANISM: Artificial Sequence
<220> FEATURE:
<223> OTHER INFORMATION: unnamed protein product

<400> SEQUENCE: 5
```

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Tyr Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215

```
<210> SEQ ID NO 6
<211> LENGTH: 219
<212> TYPE: PRT
<213> ORGANISM: Artificial Sequence
<220> FEATURE:
<223> OTHER INFORMATION: unnamed protein product

<400> SEQUENCE: 6
```

Asp Val Leu Met Thr Gln Thr Pro Leu Ser Leu Pro Val Ser Leu Gly
1               5                   10                  15

Asp Gln Ala Ser Leu Ser Cys Arg Ser Ser Gln Tyr Leu Val His Ser
            20                  25                  30

Asn Gly Asn Thr Tyr Leu Glu Trp Tyr Leu Gln Lys Pro Gly Gln Ser
        35                  40                  45

Pro Lys Leu Leu Leu Tyr Lys Val Ser Asn Arg Phe Ser Gly Val Pro
    50                  55                  60

Asp Arg Phe Ser Gly Ser Gly Ser Gly Thr Asp Phe Thr Leu Lys Leu
65                  70                  75                  80

Ser Arg Val Glu Ala Glu Asp Leu Gly Val Tyr Tyr Cys Phe Gln Gly
                85                  90                  95

```
Ser His Val Pro Leu Thr Phe Gly Ala Gly Thr Lys Leu Glu Leu Lys
            100                 105                 110

Arg Ala Asp Ala Ala Pro Thr Val Ser Leu Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Leu Asn Val Lys Trp Lys Leu Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Leu Val Lys Ser Phe Asn Arg Asn Glu Cys
    210                 215
```

<210> SEQ ID NO 7
<211> LENGTH: 441
<212> TYPE: PRT
<213> ORGANISM: Artificial Sequence
<220> FEATURE:
<223> OTHER INFORMATION: unnamed protein product

<400> SEQUENCE: 7

```
Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Leu Gly Tyr
            20                  25                  30

Gly Val Asn Trp Val Arg Gln Pro Pro Gly Gln Gly Leu Glu Trp Leu
        35                  40                  45

Met Gly Ile Trp Gly Asp Gly Ser Thr Asp Tyr Asn Ser Ala Leu Lys
    50                  55                  60

Ser Arg Ile Ser Ile Thr Lys Asp Asn Ser Lys Ser Gln Val Phe Leu
65                  70                  75                  80

Lys Met Asn Ser Leu Gln Thr Asp Asp Thr Ala Lys Tyr Tyr Cys Thr
                85                  90                  95

Arg Ala Pro Tyr Gly Lys Gln Tyr Phe Ala Tyr Trp Gly Gln Gly Thr
            100                 105                 110

Leu Val Thr Val Ser Ala Ala Lys Thr Thr Pro Pro Ser Val Tyr Pro
        115                 120                 125

Leu Ala Pro Gly Ser Ala Ala Gln Thr Asp Ser Met Val Thr Leu Gly
    130                 135                 140

Cys Leu Val Lys Gly Tyr Phe Pro Glu Pro Val Thr Val Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Pro Ser Ser Thr
            180                 185                 190

Trp Pro Ser Glu Thr Val Thr Cys Asn Val Ala His Pro Ala Ser Ser
        195                 200                 205

Thr Lys Val Asp Lys Lys Ile Val Pro Arg Asp Cys Gly Cys Lys Pro
    210                 215                 220

Cys Ile Cys Thr Val Pro Glu Val Ser Ser Val Phe Ile Phe Pro Pro
225                 230                 235                 240
```

```
Lys Pro Lys Asp Val Leu Thr Ile Thr Leu Thr Pro Lys Val Thr Cys
            245                 250                 255

Val Val Val Asp Ile Ser Lys Asp Asp Pro Glu Val Gln Phe Ser Trp
            260                 265                 270

Phe Val Asp Asp Val Glu Val His Thr Ala His Thr Gln Pro Arg Glu
            275                 280                 285

Glu Gln Phe Asn Ser Thr Phe Arg Ser Val Ser Glu Leu Pro Ile Met
            290                 295                 300

His Gln Asp Trp Leu Asn Gly Lys Glu Phe Lys Cys Arg Val Asn Ser
305                 310                 315                 320

Ala Ala Phe Pro Ala Pro Ile Glu Lys Thr Ile Ser Lys Thr Lys Gly
            325                 330                 335

Arg Pro Lys Ala Pro Gln Val Tyr Thr Ile Pro Pro Lys Glu Gln
            340                 345                 350

Met Ala Lys Asp Lys Val Ser Leu Thr Cys Met Ile Thr Asp Phe Phe
            355                 360                 365

Pro Glu Asp Ile Thr Val Glu Trp Gln Trp Asn Gly Gln Pro Ala Glu
            370                 375                 380

Asn Tyr Lys Asn Thr Gln Pro Ile Met Asp Thr Asp Gly Ser Tyr Phe
385                 390                 395                 400

Val Tyr Ser Lys Leu Asn Val Gln Lys Ser Asn Trp Glu Ala Gly Asn
            405                 410                 415

Thr Phe Thr Cys Ser Val Leu His Glu Gly Leu His Asn His His Thr
            420                 425                 430

Glu Lys Ser Leu Ser His Ser Pro Gly
            435                 440

<210> SEQ ID NO 8
<211> LENGTH: 442
<212> TYPE: PRT
<213> ORGANISM: Artificial Sequence
<220> FEATURE:
<223> OTHER INFORMATION: unnamed protein product

<400> SEQUENCE: 8

Gln Val Gln Leu Lys Glu Ser Gly Pro Gly Leu Val Ala Pro Ser Gln
1               5                   10                  15

Ser Leu Ser Leu Thr Cys Thr Val Ser Gly Phe Ser Leu Leu Gly Tyr
            20                  25                  30

Gly Val Asn Trp Val Arg Gln Pro Pro Gly Gln Gly Leu Glu Trp Leu
        35                  40                  45

Gly Met Leu Trp Gly Asp Gly Ser Thr Asp Tyr Asn Ser Ala Leu Lys
    50                  55                  60

Ser Arg Leu Thr Leu Ser Lys Asp Asn Ser Lys Ser Gln Val Phe Leu
65                  70                  75                  80

Lys Met Asn Ser Leu Gln Thr Asp Asp Thr Ala Lys Tyr Tyr Cys Thr
                85                  90                  95

Arg Ala Pro Tyr Gly Lys Gly Ala Tyr Phe Ala Tyr Trp Gly Gln Gly
            100                 105                 110

Thr Leu Val Thr Val Ser Ala Ala Lys Thr Thr Pro Pro Ser Val Tyr
            115                 120                 125

Pro Leu Ala Pro Gly Ser Ala Ala Gln Thr Asn Ser Met Val Thr Leu
        130                 135                 140

Gly Cys Leu Val Lys Gly Tyr Phe Pro Glu Pro Val Thr Val Thr Trp
145                 150                 155                 160
```

-continued

Asn Ser Gly Ser Leu Ser Ser Gly Val His Thr Phe Pro Ala Val Leu
            165                 170                 175

Gln Ser Asp Leu Tyr Thr Leu Ser Ser Val Thr Val Pro Ser Ser
        180                 185                 190

Thr Trp Pro Ser Glu Thr Val Thr Cys Asn Val Ala His Pro Ala Ser
            195                 200                 205

Ser Thr Lys Val Asp Lys Lys Leu Val Pro Arg Asp Cys Gly Cys Lys
        210                 215                 220

Pro Cys Leu Cys Thr Val Pro Glu Val Ser Ser Val Phe Leu Phe Pro
225                 230                 235                 240

Pro Lys Pro Lys Asp Val Leu Thr Leu Thr Pro Lys Val Thr
            245                 250                 255

Cys Val Val Val Asp Leu Ser Lys Asp Pro Glu Val Gln Phe Ser
        260                 265                 270

Trp Phe Val Asp Asp Val Glu Val His Thr Ala Gln Thr Lys Pro Arg
            275                 280                 285

Glu Glu Gln Phe Asn Ser Thr Phe Arg Ser Val Ser Glu Leu Pro Leu
        290                 295                 300

Met His Gln Asp Trp Leu Asn Gly Lys Glu Phe Lys Cys Arg Val Asn
305                 310                 315                 320

Ser Ala Ala Phe Pro Ala Pro Leu Glu Lys Thr Leu Ser Lys Thr Lys
                325                 330                 335

Gly Arg Pro Lys Ala Pro Gln Val Tyr Thr Leu Pro Pro Lys Glu
            340                 345                 350

Gln Met Ala Lys Asp Lys Val Ser Leu Thr Cys Met Leu Thr Asp Phe
        355                 360                 365

Phe Pro Glu Asp Leu Thr Val Glu Trp Gln Trp Asn Gly Gln Pro Ala
    370                 375                 380

Glu Asn Tyr Lys Asn Thr Gln Pro Leu Met Asp Thr Asp Gly Ser Tyr
385                 390                 395                 400

Phe Val Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
            420                 425                 430

Thr Glu Lys Ser Leu Ser His Ser Pro Gly
        435                 440

<210> SEQ ID NO 9
<211> LENGTH: 446
<212> TYPE: PRT
<213> ORGANISM: Artificial Sequence
<220> FEATURE:
<223> OTHER INFORMATION: unnamed protein product

<400> SEQUENCE: 9

Glu Val Pro Leu Lys Glu Ser Gly Pro Thr Leu Val Lys Pro Thr Gln
1               5                   10                  15

Thr Leu Thr Leu Thr Cys Ser Phe Ser Gly Phe Ser Leu Thr Thr Asp
                20                  25                  30

Glu Val Gly Val Ala Trp Ile Arg Gln Pro Pro Gly Lys Ala Leu Glu
            35                  40                  45

Trp Leu Ala Val Leu Tyr Gly Asp Asp Asp Lys Arg Tyr Ser Pro Ser
        50                  55                  60

-continued

```
Leu Lys Ser Arg Leu Ser Ile Thr Lys Asp Ser Ser Lys Asn Gln Val
 65                  70                  75                  80

Val Leu Thr Met Thr Ser Leu Asp Pro Val Asp Thr Gly Thr Tyr Tyr
                 85                  90                  95

Cys Ala His Thr Arg Asp Tyr Phe Asp Tyr Trp Gly Gln Gly Thr Leu
            100                 105                 110

Leu Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Leu Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Leu Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Leu Glu Lys Thr Leu
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Leu Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 10
<211> LENGTH: 454
<212> TYPE: PRT
<213> ORGANISM: Artificial Sequence
<220> FEATURE:
<223> OTHER INFORMATION: unnamed protein product
```

<400> SEQUENCE: 10

```
Gln Val Pro Leu Lys Glu Ser Gly Pro Thr Leu Val Lys Pro Thr Gln
1               5                   10                  15

Thr Leu Thr Leu Thr Cys Ser Phe Gly Ser Phe Ser Leu Thr Thr Asp
            20                  25                  30

Glu Val Gly Val Ala Trp Leu Arg Gln Pro Pro Gly Lys Ala Leu Glu
        35                  40                  45

Trp Val Ala Leu Leu Tyr Gly Asn Asp Lys Arg Tyr Ser Pro Ser
    50                  55                  60

Leu Lys Ser Arg Leu Ser Leu Thr Lys Asp Ser Ser Lys Asn Gln Val
65                  70                  75                  80

Val Leu Thr Met Thr Ser Leu Asp Pro Val Asp Thr Gly Thr Tyr Tyr
                85                  90                  95

Cys Ala His Thr Arg Asp Tyr Thr Asp Tyr Val Trp Thr Tyr Tyr Phe
            100                 105                 110

Asp Tyr Trp Gly Gln Gly Thr Leu Leu Thr Val Ser Ser Ala Ser Thr
        115                 120                 125

Lys Asn Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Leu Cys
        195                 200                 205

Asn Val Asn His Lys Pro Ser Asn Thr Lys Val Asp Lys Arg Val Glu
            210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Leu Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Leu Glu Lys Thr Leu Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
370                 375                 380

Leu Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415
```

Lys Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
                435                 440                 445

Leu Ser Leu Ser Pro Gly
            450

<210> SEQ ID NO 11
<211> LENGTH: 219
<212> TYPE: PRT
<213> ORGANISM: Artificial Sequence
<220> FEATURE:
<223> OTHER INFORMATION: unnamed protein product

<400> SEQUENCE: 11

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Tyr Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215

<210> SEQ ID NO 12
<211> LENGTH: 217
<212> TYPE: PRT
<213> ORGANISM: Artificial Sequence
<220> FEATURE:
<223> OTHER INFORMATION: unnamed protein product

<400> SEQUENCE: 12

Asp Val Leu Met Thr Gln Thr Pro Leu Ser Leu Pro Val Ser Leu Gly
1               5                   10                  15

Asp Gln Ala Ser Leu Ser Cys Arg Ser Ser Gln Tyr Leu Val His Ser
            20                  25                  30

Asn Gly Asn Thr Tyr Leu Glu Trp Tyr Leu Gln Lys Pro Gly Gln Ser
        35                  40                  45

Pro Lys Leu Leu Tyr Lys Val Ser Asn Arg Phe Ser Gly Val Pro
 50                  55                  60

Asp Arg Phe Ser Gly Ser Gly Thr Asp Phe Thr Leu Lys Leu Ser Arg
65                  70                  75                  80

Val Glu Ala Glu Asp Leu Gly Val Tyr Tyr Cys Phe Gln Gly Ser His
                 85                  90                  95

Val Pro Leu Thr Phe Gly Ala Gly Thr Lys Leu Glu Leu Lys Arg Ala
            100                 105                 110

Asp Ala Ala Pro Thr Val Ser Leu Phe Pro Pro Ser Ser Glu Gln Leu
        115                 120                 125

Thr Ser Gly Gly Ala Ser Val Val Cys Phe Leu Asn Asn Phe Tyr Pro
130                 135                 140

Lys Asp Leu Asn Val Lys Trp Lys Leu Asp Gly Ser Glu Arg Gln Asn
145                 150                 155                 160

Gly Val Leu Asn Ser Trp Thr Asp Gln Asp Ser Lys Asp Ser Thr Tyr
                165                 170                 175

Ser Met Ser Ser Thr Leu Thr Leu Thr Lys Asp Glu Tyr Glu Arg His
            180                 185                 190

Asn Ser Tyr Thr Cys Glu Ala Thr His Lys Thr Ser Thr Ser Pro Leu
        195                 200                 205

Val Lys Ser Phe Asn Arg Asn Glu Cys
210                 215

<210> SEQ ID NO 13
<211> LENGTH: 441
<212> TYPE: PRT
<213> ORGANISM: Artificial Sequence
<220> FEATURE:
<223> OTHER INFORMATION: unnamed protein product

<400> SEQUENCE: 13

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Leu Gly Tyr
            20                  25                  30

Gly Val Asn Trp Val Arg Gln Pro Pro Gly Gln Gly Leu Glu Trp Leu
        35                  40                  45

Met Gly Ile Trp Gly Asp Gly Ser Thr Asp Tyr Asn Ser Ala Leu Lys
    50                  55                  60

Ser Arg Ile Ser Ile Thr Lys Asp Asn Ser Lys Ser Gln Val Phe Leu
65                  70                  75                  80

Lys Met Asn Ser Leu Gln Thr Asp Asp Thr Ala Lys Tyr Tyr Cys Thr
                85                  90                  95

Arg Ala Pro Tyr Gly Lys Gln Tyr Phe Ala Tyr Trp Gly Gln Gly Thr
            100                 105                 110

Leu Val Thr Val Ser Ala Ala Lys Thr Thr Pro Pro Ser Val Tyr Pro
        115                 120                 125

Leu Ala Pro Gly Ser Ala Ala Gln Thr Asp Ser Met Val Thr Leu Gly
130                 135                 140

Cys Leu Val Lys Gly Tyr Phe Pro Glu Pro Val Thr Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Val Thr Val Pro Ser Ser Thr
            180                 185                 190

Trp Pro Ser Glu Thr Val Thr Cys Asn Val Ala His Pro Ala Ser Ser
            195                 200                 205

Thr Lys Val Asp Lys Lys Ile Val Pro Arg Asp Cys Gly Cys Lys Pro
    210                 215                 220

Cys Ile Cys Thr Val Pro Glu Val Ser Ser Val Phe Ile Phe Pro Pro
225                 230                 235                 240

Lys Pro Lys Asp Val Leu Thr Ile Thr Leu Thr Pro Lys Val Thr Cys
            245                 250                 255

Val Val Val Asp Ile Ser Lys Asp Asp Pro Glu Val Gln Phe Ser Trp
            260                 265                 270

Phe Val Asp Asp Val Glu Val His Thr Ala His Thr Gln Pro Arg Glu
            275                 280                 285

Glu Gln Phe Asn Ser Thr Phe Arg Ser Val Ser Glu Leu Pro Ile Met
            290                 295                 300

His Gln Asp Trp Leu Asn Gly Lys Glu Phe Lys Cys Arg Val Asn Ser
305                 310                 315                 320

Ala Ala Phe Pro Ala Pro Ile Glu Lys Thr Ile Ser Lys Thr Lys Gly
            325                 330                 335

Arg Pro Lys Ala Pro Gln Val Tyr Thr Ile Pro Pro Pro Lys Glu Gln
            340                 345                 350

Met Ala Lys Asp Lys Val Ser Leu Thr Cys Met Ile Thr Asp Phe Phe
            355                 360                 365

Pro Glu Asp Ile Thr Val Glu Trp Gln Trp Asn Gly Gln Pro Ala Glu
            370                 375                 380

Asn Tyr Lys Asn Thr Gln Pro Ile Met Asp Thr Asp Gly Ser Tyr Phe
385                 390                 395                 400

Val Tyr Ser Lys Leu Asn Val Gln Lys Ser Asn Trp Glu Ala Gly Asn
            405                 410                 415

Thr Phe Thr Cys Ser Val Leu His Glu Gly Leu His Asn His His Thr
            420                 425                 430

Glu Lys Ser Leu Ser His Ser Pro Gly
            435                 440

<210> SEQ ID NO 14
<211> LENGTH: 453
<212> TYPE: PRT
<213> ORGANISM: Artificial Sequence
<220> FEATURE:
<223> OTHER INFORMATION: unnamed protein product

<400> SEQUENCE: 14

Gln Val Gln Leu Lys Glu Ser Gly Pro Gly Leu Val Ala Pro Ser Gln
1               5                   10                  15

Ser Leu Ser Leu Thr Cys Thr Val Ser Gly Phe Ser Leu Leu Gly Tyr
            20                  25                  30

Asn His His Gln Met Met Cys Leu Ser Leu Gly Tyr Gly Val Asn Trp
            35                  40                  45

Val Arg Gln Pro Pro Gly Gln Gly Leu Glu Trp Leu Gly Met Leu Trp
    50                  55                  60

Gly Asp Gly Ser Thr Asp Tyr Asn Ser Ala Leu Lys Ser Arg Leu Thr
65                  70                  75                  80

Leu Ser Lys Asp Asn Ser Lys Ser Gln Val Phe Leu Lys Met Asn Ser
            85                  90                  95

```
Leu Gln Thr Asp Asp Thr Ala Lys Tyr Tyr Cys Thr Arg Ala Pro Tyr
                100                 105                 110

Gly Lys Gln Tyr Phe Ala Tyr Trp Gly Gln Gly Thr Leu Val Thr Val
            115                 120                 125

Ser Ala Ala Lys Thr Thr Pro Pro Ser Val Tyr Pro Leu Ala Pro Gly
        130                 135                 140

Ser Ala Ala Gln Thr Asn Ser Met Val Thr Leu Gly Cys Leu Val Lys
145                 150                 155                 160

Gly Tyr Phe Pro Glu Pro Val Thr Val Thr Trp Asn Ser Gly Ser Leu
                165                 170                 175

Ser Ser Gly Val His Thr Phe Pro Ala Val Leu Gln Ser Asp Leu Tyr
            180                 185                 190

Thr Leu Ser Ser Ser Val Thr Val Pro Ser Ser Thr Trp Pro Ser Glu
        195                 200                 205

Thr Val Thr Cys Asn Val Ala His Pro Ala Ser Ser Thr Lys Val Asp
210                 215                 220

Lys Lys Leu Val Pro Arg Asp Cys Gly Cys Lys Pro Cys Leu Cys Thr
225                 230                 235                 240

Val Pro Glu Val Ser Ser Val Phe Leu Phe Pro Pro Lys Pro Lys Asp
                245                 250                 255

Val Leu Thr Leu Thr Leu Thr Pro Lys Val Thr Cys Val Val Val Asp
            260                 265                 270

Leu Ser Lys Asp Asp Pro Glu Val Gln Phe Ser Trp Phe Val Asp Asp
        275                 280                 285

Val Glu Val His Thr Ala Gln Thr Lys Pro Arg Glu Glu Gln Phe Asn
290                 295                 300

Ser Thr Phe Arg Ser Val Ser Glu Leu Pro Leu Met His Gln Asp Trp
305                 310                 315                 320

Leu Asn Gly Lys Glu Phe Lys Cys Arg Val Asn Ser Ala Ala Phe Pro
                325                 330                 335

Ala Pro Leu Glu Lys Thr Leu Ser Lys Thr Lys Gly Arg Pro Lys Ala
            340                 345                 350

Pro Gln Val Tyr Thr Leu Pro Pro Lys Glu Gln Met Ala Lys Asp
        355                 360                 365

Lys Val Ser Leu Thr Cys Met Leu Thr Asp Phe Phe Pro Glu Asp Leu
370                 375                 380

Thr Val Glu Trp Gln Trp Asn Gly Gln Pro Ala Glu Asn Tyr Lys Asn
385                 390                 395                 400

Thr Gln Pro Leu Met Asp Thr Asp Gly Ser Tyr Phe Val Tyr Ser Lys
                405                 410                 415

Leu Asn Val Gln Lys Ser Asn Trp Glu Ala Gly Asn Thr Phe Thr Cys
            420                 425                 430

Ser Val Leu His Glu Gly Leu His Asn His His Thr Glu Lys Ser Leu
        435                 440                 445

Ser His Ser Pro Gly
    450

<210> SEQ ID NO 15
<211> LENGTH: 216
<212> TYPE: PRT
<213> ORGANISM: Artificial Sequence
<220> FEATURE:
<223> OTHER INFORMATION: unnamed protein product
```

-continued

```
<400> SEQUENCE: 15

Glu Leu Val Leu Thr Gln Ser Pro Ala Ser Leu Ser Ile Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln His Lys Pro Gly Gln Ala Pro Arg Ile Leu Ile
        35                  40                  45

Tyr Asp Ala Ser Thr Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Ile Tyr Tyr Cys Gln Gln Arg Ser Asn Trp Pro Pro
                85                  90                  95

Ser Phe Thr Phe Gly Pro Gly Thr Arg Val Asp Leu Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Ile Gln Ser Gly Asn
145                 150                 155                 160

Ser Gln Glu Ser Val Thr Glu Gln Asp Ser Lys Asp Ser Thr Tyr Ser
                165                 170                 175

Ile Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 16
<211> LENGTH: 216
<212> TYPE: PRT
<213> ORGANISM: Artificial Sequence
<220> FEATURE:
<223> OTHER INFORMATION: unnamed protein product

<400> SEQUENCE: 16

Glu Leu Val Leu Thr Gln Ser Pro Ala Ser Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln His Lys Pro Gly Gln Ala Pro Arg Leu Leu Leu
        35                  40                  45

Tyr Asp Ala Ser Thr Arg Ala Thr Gly Leu Pro Ala Arg Phe Ser Gly
    50                  55                  60

Ser Gly Ser Gly Thr Asp Phe Thr Leu Thr Leu Ser Ser Leu Glu Pro
65                  70                  75                  80

Glu Asp Phe Ala Leu Tyr Tyr Cys Gln Gln Arg Ser Asn Trp Pro Pro
                85                  90                  95

Ser Phe Thr Phe Gly Pro Gly Thr Arg Val Asp Leu Lys Arg Thr Val
            100                 105                 110

Ala Ala Pro Ser Val Phe Leu Phe Pro Pro Ser Asp Glu Gln Leu Lys
        115                 120                 125
```

```
Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 17
<211> LENGTH: 16
<212> TYPE: PRT
<213> ORGANISM: Artificial Sequence
<220> FEATURE:
<223> OTHER INFORMATION: example

<400> SEQUENCE: 17

Pro Glu Ala Cys Asp Glu Phe Gly Pro Pro Glu Ala Asp Lys Thr Arg
1               5                   10                  15

<210> SEQ ID NO 18
<211> LENGTH: 7
<212> TYPE: PRT
<213> ORGANISM: Artificial Sequence
<220> FEATURE:
<223> OTHER INFORMATION: example

<400> SEQUENCE: 18

Cys Asp Glu Phe Gly Pro Pro
1               5

<210> SEQ ID NO 19
<211> LENGTH: 6
<212> TYPE: PRT
<213> ORGANISM: Artificial Sequence
<220> FEATURE:
<223> OTHER INFORMATION: example

<400> SEQUENCE: 19

Cys Asp Glu Phe Gly Pro
1               5

<210> SEQ ID NO 20
<211> LENGTH: 7
<212> TYPE: PRT
<213> ORGANISM: Artificial Sequence
<220> FEATURE:
<223> OTHER INFORMATION: example

<400> SEQUENCE: 20

Ala Cys Asp Glu Phe Gly Pro
1               5

<210> SEQ ID NO 21
<211> LENGTH: 6
<212> TYPE: PRT
<213> ORGANISM: Artificial Sequence
<220> FEATURE:
<223> OTHER INFORMATION: example
```

-continued

```
<400> SEQUENCE: 21

Asp Glu Phe Gly Pro Pro
1               5

<210> SEQ ID NO 22
<211> LENGTH: 7
<212> TYPE: PRT
<213> ORGANISM: Artificial Sequence
<220> FEATURE:
<223> OTHER INFORMATION: example

<400> SEQUENCE: 22

Asp Glu Phe Gly Pro Pro Glu
1               5

<210> SEQ ID NO 23
<211> LENGTH: 6
<212> TYPE: PRT
<213> ORGANISM: Artificial Sequence
<220> FEATURE:
<223> OTHER INFORMATION: example

<400> SEQUENCE: 23

Cys Asp Glu Phe Gly Pro
1               5

<210> SEQ ID NO 24
<211> LENGTH: 6
<212> TYPE: PRT
<213> ORGANISM: Artificial Sequence
<220> FEATURE:
<223> OTHER INFORMATION: example

<400> SEQUENCE: 24

Asp Glu Phe Gly Pro Pro
1               5
```